(12) United States Patent
Saito et al.

(10) Patent No.: US 9,359,553 B2
(45) Date of Patent: Jun. 7, 2016

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Masayuki Saito, Chiba (JP); Yoshimasa Furusato, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/552,496

(22) Filed: Nov. 25, 2014

(65) Prior Publication Data

US 2015/0240160 A1 Aug. 27, 2015

(30) Foreign Application Priority Data

Feb. 25, 2014 (JP) .................. 2014-033988
Oct. 2, 2014 (JP) .................. 2014-203753

(51) Int. Cl.
| | |
|---|---|
| *C09K 19/34* | (2006.01) |
| *C09K 19/30* | (2006.01) |
| *C09K 19/14* | (2006.01) |
| *C07C 15/18* | (2006.01) |
| *C07C 13/28* | (2006.01) |
| *C09K 19/12* | (2006.01) |

(52) U.S. Cl.
CPC ............ *C09K 19/3402* (2013.01); *C07C 13/28* (2013.01); *C07C 15/18* (2013.01); *C09K 19/14* (2013.01); *C09K 19/3003* (2013.01); *C09K 19/3028* (2013.01); *C07C 2101/14* (2013.01); *C09K 2019/122* (2013.01); *C09K 2019/301* (2013.01); *C09K 2019/3004* (2013.01); *C09K 2019/3016* (2013.01); *C09K 2019/3027* (2013.01); *C09K 2019/3078* (2013.01); *C09K 2019/3422* (2013.01); *C09K 2019/3425* (2013.01)

(58) Field of Classification Search
CPC ........... C09K 19/3402; C09K 19/3028; C09K 19/3003; C09K 19/14; C09K 2019/3422; C09K 2019/3425; C09K 2019/122; C09K 2019/3004; C09K 2019/301; C09K 2019/3016; C09K 2019/3027; C09K 2019/3028; C07C 15/18; C07C 2101/14; C07C 13/28
USPC ............. 252/299.01, 299.61, 299.63, 299.66; 428/1.1; 349/182, 183; 570/129; 585/25

See application file for complete search history.

(56) References Cited

U.S. PATENT DOCUMENTS

| | | | |
|---|---|---|---|
| 5,093,026 A | 3/1992 | Bishop et al. | |
| 8,916,063 B2 * | 12/2014 | Goto | C09K 19/12 252/299.61 |

FOREIGN PATENT DOCUMENTS

JP H03-503651 8/1991

* cited by examiner

*Primary Examiner* — Geraldina Visconti
(74) *Attorney, Agent, or Firm* — Jianq Chyun IP Office

(57) ABSTRACT

A liquid crystal composition and an AM LCD device containing the liquid crystal composition are described. The liquid crystal composition has a negative dielectric anisotropy, includes a specific compound having a high maximum temperature and a large optical anisotropy as a first component, and may also include at least one of a specific compound having a large negative dielectric anisotropy as a second component, a specific compound having a high maximum temperature or a small viscosity as a third component, and a specific compound having a polymerizable group as an additive component.

16 Claims, No Drawings

LIQUID CRYSTAL COMPOSITION AND LIQUID CRYSTAL DISPLAY DEVICE

CROSS-REFERENCE TO RELATED APPLICATION

This application claims the priority benefit of Japan application serial no. 2014-033988, filed on Feb. 25, 2014. The entirety of the above-mentioned patent application is hereby incorporated by reference herein and made a part of this specification.

TECHNICAL FIELD

The invention relates to a liquid crystal composition, a liquid crystal display device including this composition and so forth, and particularly relates to a liquid crystal composition having a negative dielectric anisotropy and a liquid crystal display (LCD) device including this composition and having a mode such as IPS, VA, FFS or FPA. The invention also relates to an LCD device of a polymer sustained alignment (PSA) type.

TECHNICAL BACKGROUND

For LCD devices, a classification based on the operating mode of liquid crystal molecules includes modes such as PC (phase change), TN (twisted nematic), STN (super twisted nematic), ECB (electrically controlled birefringence), OCB (optically compensated bend), IPS (in-plane switching), VA (vertical alignment), FFS (fringe field switching) and FPA (field-induced photo-reactive alignment). A classification based on the driving mode of the device includes PM (passive matrix) and AM (active matrix) types. The PM types are classified into static type, multiplex type and so forth, and the AM types are classified into TFT (thin film transistor) type, MIM (metal-insulator-metal) type and so forth. The TFT type is further classified into amorphous silicon and polycrystal silicon types. The latter is classified into a high temperature type and a low temperature type depending on the production process. A classification based on the light source includes a reflection type utilizing natural light, a transmission type utilizing a backlight, and a semi-transmission type utilizing both natural light and a backlight.

The LCD device includes a liquid crystal composition having a nematic phase. The composition has suitable characteristics. An AM device having good characteristics can be achieved by improving the characteristics of the composition. Table 1 below summarizes the relationship between the two groups of characteristics. The characteristics of the composition will be further described on the basis of a commercially available AM device. The temperature range of nematic phase relates to the temperature range in which the device can be used. A desirable maximum temperature of nematic phase is about 70° C. or higher and a desirable minimum temperature of nematic phase is about −10° C. or lower. The viscosity of the composition relates to the response time of the device. A short response time is desirable for displaying moving images on the device. A response time that is one millisecond shorter than that of other devices is desirable. Thus, a small viscosity of the composition is desirable. A small viscosity at a low temperature is more desirable.

TABLE 1

Characteristics of Composition and AM Devices

| No. | Characteristics of Composition | Characteristics of AM Device |
| --- | --- | --- |
| 1 | Wide temperature range of nematic phase | Wide temperature range in which the device can be used |
| 2 | Small viscosity [1] | Short response time |
| 3 | Suitable optical anisotropy | Large contrast ratio |
| 4 | Large positive or negative dielectric anisotropy | Low threshold voltage and small electric power consumption, Large contrast ratio |
| 5 | Large specific resistance | Large voltage holding ratio, and large contrast ratio |
| 6 | High stability to UV light and heat | Long service life |

[1] A composition can be injected in an LCD device in a shorter period of time.

The optical anisotropy ($\Delta n$) of the composition relates to the contrast ratio of the device. A large optical anisotropy or a small optical anisotropy, namely a suitable optical anisotropy, is needed, depending on the mode of the device. The product ($\Delta n \times d$) of the $\Delta n$ of the composition and the cell gap (d) of the device is designed so as to maximize the contrast ratio. A suitable value of the product depends on the type of the operating mode. This value is in a range of about 0.30 μm to about 0.40 μm for a device of a VA mode, and in a range of about 0.20 μm to about 0.30 μm for a device of an IPS mode or an FFS mode. In these cases, a composition having a large $\Delta n$ is desirable for a device with a small cell gap. A large dielectric anisotropy ($\Delta \in$) of the composition contributes to a low threshold voltage, low power consumption and a large contrast ratio of the device. A large $\Delta \in$ is thus desirable. A large specific resistance of the composition contributes to a large voltage holding ratio and a large contrast ratio of the device. It is thus desirable that a composition has a large specific resistance at a high temperature as well as at room temperature in an initial stage. It is desirable that a composition also has a large specific resistance at a high temperature as well as at room temperature, after it has been used for a long time. The stability of the composition to ultraviolet (UV) light and heat relates to the service life of the device. The device has a long service life when the stability is high. Such characteristics are desirable for an AM device used for a liquid crystal projector, a liquid crystal television and so forth.

A liquid crystal composition including a polymer is used for an LCD device of a polymer sustained alignment (PSA) type. First, a composition to which a small amount of a polymerizable compound has been added is poured into a device. Next, the composition is irradiated with UV light, while a voltage is applied between the substrates of the device, to polymerize the polymerizable compound and give a network structure of a polymer in the composition. In this composition, the polymer makes it possible to adjust the orientation of liquid crystal molecules, and thus the response time of the device is decreased and image burn-in is reduced. Such effects of the polymer can be expected for a device having a mode such as TN, ECB, OCB, IPS, VA, FFS or FPA.

A composition having a positive $\Delta \in$ is used for an AM device of a TN mode. A composition having a negative $\Delta \in$ is used for an AM device of a VA mode. A composition having a positive or negative $\Delta \in$ is used for an AM device of an IPS mode or FFS mode. A composition having a positive or negative $\Delta \in$ is used for an AM device of a PSA mode. Examples of the liquid crystal composition having a negative $\Delta \in$ are disclosed in the following Patent document No. 1.

Patent document No. 1: JP H03-503651 A (1991).

SUMMARY OF THE INVENTION

Accordingly, the invention provides a liquid crystal composition that satisfies at least one of characteristics such as a high maximum temperature of nematic phase, a low minimum temperature of nematic phase, a small viscosity, a suitable optical anisotropy, a large negative dielectric anisotropy, a large specific resistance, a high stability to UV light and a high stability to heat, or a liquid crystal composition that is suitably balanced between at least two of the characteristics. The invention also provides an LCD device including such a composition. The invention further provides an AM device that has characteristics such as a short response time, a large voltage holding ratio, a low threshold voltage, a large contrast ratio and a long service life.

The liquid crystal composition of the invention has a negative $\Delta\in$, and includes at least one compound selected from the group of compounds represented by formula (1) as a first component.

The LCD device of the invention includes this composition.

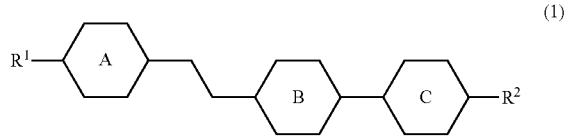

(1)

In formula (1), $R^1$ and $R^2$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen; and ring A, ring B and ring C are independently 1,4-phenylene, or 1,4-phenylene in which at least one hydrogen has been replaced by fluorine or chlorine.

The liquid crystal composition of the invention satisfies at least one of characteristics such as a high maximum temperature of nematic phase, a low minimum temperature of nematic phase, a small viscosity, a suitable optical anisotropy, a large negative dielectric anisotropy, a large specific resistance, a high stability to UV light and a high stability to heat, or is suitably balanced between at least two of the characteristics. The LCD device of the invention includes such a composition. The AM device of the invention has characteristics such as a short response time, a large voltage holding ratio, a low threshold voltage, a large contrast ratio and a long service life.

EMBODIMENTS OF THE INVENTION

The usage of the terms in the specification and claims is described below. "Liquid crystal composition" and "LCD device" are often abbreviated to "composition" and "device," respectively. "LCD device" is a generic term for a LCD panel and a LCD module. "Liquid crystal compound" is a generic term for a compound having a liquid crystal phase such as a nematic phase or a smectic phase, and for a compound having no liquid crystal phases but being mixed with a composition to adjust characteristics such as the temperature range of nematic phase, viscosity and $\Delta\in$. Such compound has a six-membered ring such as 1,4-cyclohexylene or 1,4-phenylene, and a rod-like molecular structure. A polymerizable compound is a compound that is added to a composition in order to form a polymer in it.

A liquid crystal composition is prepared by mixing plural liquid crystal compounds. The proportion of a liquid crystal compound (content) is expressed as a percentage by weight (wt %) based on the weight of this liquid crystal composition. An additive such as an optically active compound, an antioxidant, a UV light absorbent, a coloring matter, an antifoaming agent, a polymerizable compound, a polymerization initiator and a polymerization inhibitor is added to this composition as required. The proportion (added amount) of the additive is expressed as a weight percentage (wt %) based on the weight of the liquid crystal composition as in the case of the liquid crystal compound. Weight parts per million (ppm) is sometimes used. The proportion of the polymerization initiator or polymerization inhibitor is exceptionally expressed on the basis of the weight of the polymerizable compound.

"Higher limit of the temperature range of a nematic phase" is often abbreviated to "maximum temperature." "Lower limit of the temperature range of a nematic phase" is often abbreviated to "minimum temperature." That "specific resistance is large" means that a composition has a large specific resistance at a temperature close to the maximum temperature of nematic phase as well as at room temperature in an initial stage, and that the composition has a large specific resistance at a temperature close to the maximum temperature of nematic phase as well as at room temperature, after it has been used for a long time. That "a voltage holding ratio is large" means that a device has a large voltage holding ratio at a temperature close to the maximum temperature of nematic phase as well as at room temperature in an initial stage, and that the device has a large voltage holding ratio at a temperature close to the maximum temperature of nematic phase as well as at room temperature, after it has been used for a long time. The expression "increase the dielectric anisotropy" means that its value increases positively when the composition has a positive $\Delta\in$, and that its value increases negatively when the composition has a negative $\Delta\in$.

The expression "at least one 'A'" means that the number of 'A' is arbitrary. The expression "at least one 'A' may be replaced by 'B'" means that the position of 'A' is arbitrary when the number of 'A' is one, and the positions can be selected without restriction when the number of 'A' is two or more. This rule also applies to the expression "at least one 'A' has been replaced by 'B'."

In formulae (1) to (4), a symbol such as A, B or C surrounded by a hexagonal shape corresponds to a ring such as ring A, ring B or ring C. In formula (4), an oblique line crossing a hexagonal shape of ring K means that the bonding positions of a $P^1$-$Sp^1$ group on the ring can be arbitrarily selected. The same rule applies to a $P^2$-$Sp^2$ group on ring L, for instance. A subscript such as h means the number of groups bonded to ring K or the like. Two $P^1$-$Sp^1$ groups are present when h is 2. Two groups represented by $P^1$-$Sp^1$ may be the same or different. The same rule applies to arbitrary two groups represented by $P^1$-$Sp^1$ when h is greater than 2. The same rule also applies to other groups. A compound represented by formula (1) is sometimes abbreviated to compound (1). This abbreviation applies to a compound represented by formula (2) or the like. Compound (1) means one compound, a mixture of two compounds, or a mixture of three or more compounds represented by formula (1).

A symbol for a terminal group, $R^1$, is used for a plurality of compounds in the chemical formulae of component compounds, where two groups represented by arbitrary two $R^1$ may be the same or be different. In one case, for example, $R^1$ of compound (1-1) is ethyl and $R^1$ of compound (1-2) is ethyl. In another case, $R^1$ of compound (1-1) is ethyl and $R^1$ of compound (1-2) is propyl. The same rule applies to other symbols for other terminal groups and so on. In formula (2), two rings D are present when a is 2. In this compound, two groups represented by two rings D may be the same or different. The same rule applies to arbitrary two rings D, as a is greater than 2. The same rule also applies to symbols such as $Z^1$ and ring G.

2-Fluoro-1,4-phenylene means any of the two divalent groups described below. The fluorine may be facing left (L) or facing right (R) in the chemical formula. The same rule also applies to an asymmetric divalent group derived from a ring, such as tetrahydropyran-2,5-diyl. The same rule also applies to a bonding group such as carbonyloxy (—COO— and —OCO—).

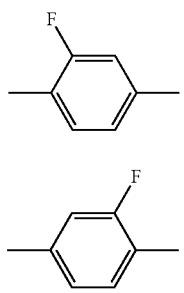

The invention includes the following items.

Item 1 is a liquid crystal composition which has a negative $\Delta\epsilon$ and includes at least one compound selected from the group of compounds represented by formula (1) as a first component:

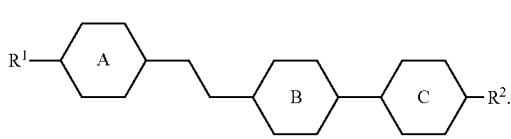

In formula (1), $R^1$ and $R^2$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen; and ring A, ring B and ring C are independently 1,4-phenylene, or 1,4-phenylene in which at least one hydrogen has been replaced by fluorine or chlorine.

Item 2 is the liquid crystal composition of item 1 which includes at least one compound selected from the group of compounds represented by formulae (1-1) to (1-4) as the first component:

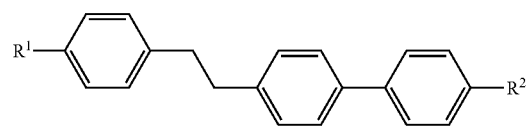

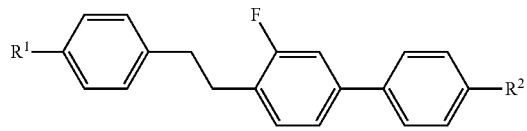

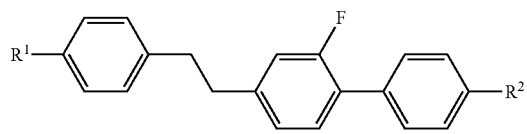

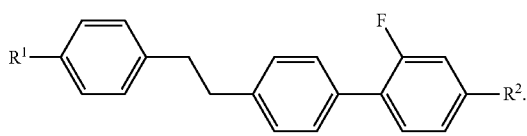

In formulae (1-1) to (1-4), $R^1$ and $R^2$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen.

Item 3 is the liquid crystal composition of item 1 or 2 in which the proportion of the first component is in the range of 3 wt % to 20 wt % based on the weight of the liquid crystal composition.

Item 4 is the liquid crystal composition of any one of items 1 to 3 which further includes at least one compound selected from the group of compounds represented by formula (2) as a $2^{nd}$ component:

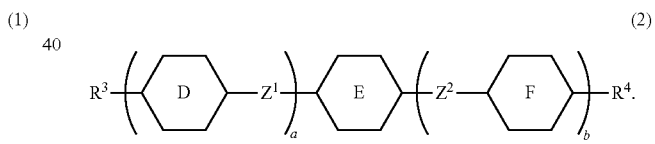

In formula (2), $R^3$ and $R^4$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen has been replaced by halogen; ring D and ring F are independently 1,4-cyclohexylene, 1,4-cyclohexenylene, 1,4-phenylene, 1,4-phenylene in which at least one hydrogen has been replaced by fluorine or chlorine, or tetrahydropyran-2,5-diyl; ring E is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^1$ and $Z^2$ are independently a single bond, ethylene, carbonyloxy or methyleneoxy; a is 1, 2 or 3; b is 0 or 1; the sum of a and b is 3 or less; and when the sum of a and b is 2, and the a-numbering ring D and the b-numbering ring F are 1,4-phenylene or 1,4-phenylene in which at least one hydrogen has been replaced by fluorine or chlorine, $Z^1$ and $Z^2$ are independently a single bond, carbonyloxy or methyleneoxy.

Item 5 is the liquid crystal composition of any one of items 1 to 4 which includes at least one compound selected from the group of compounds represented by formulae (2-1) to (2-19) as the second component:

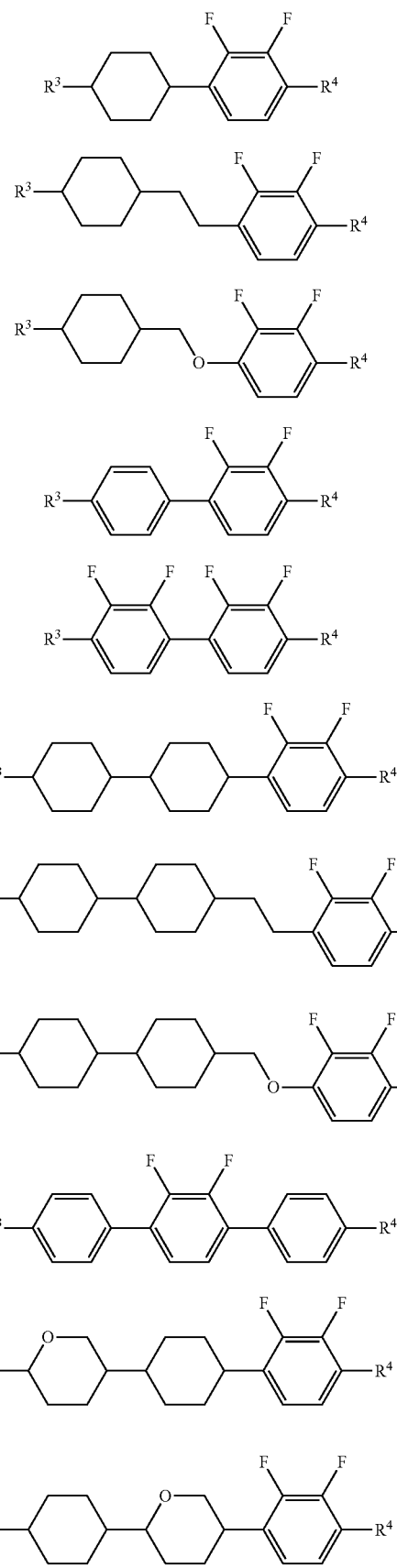
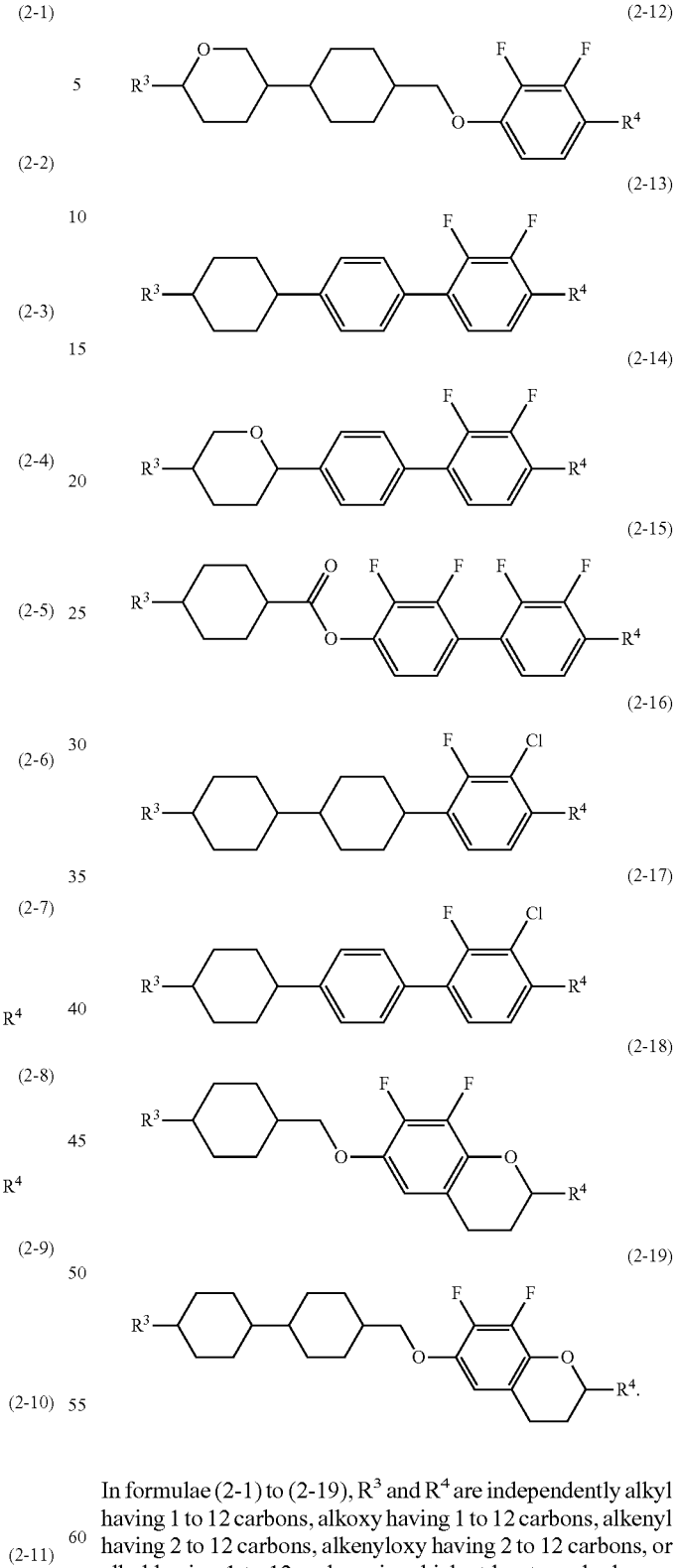

In formulae (2-1) to (2-19), $R^3$ and $R^4$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen has been replaced by halogen.

Item 6 is the liquid crystal composition of item 4 or 5 in which the proportion of the second component is in the range of 20 wt % to 70 wt % based on the weight of the liquid crystal composition.

Item 7 is the liquid crystal composition of any one of items 1 to 6 which further includes at least one compound selected from the group of compounds represented by formula (3) as a 3$^{rd}$ component:

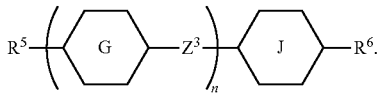

In formula (3), $R^5$ and $R^6$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen; ring G and ring J are independently 1,4-cyclohexylene, 1,4-phenylene, 2-fluoro-1,4-phenylene or 2,5-difluoro-1,4-phenylene; $Z^3$ is a single bond, ethylene or carbonyloxy; n is 1, 2 or 3; and when n is 2, and two of rings G and ring J are 1,4-phenylene, 2-fluoro-1,4-phenylene or 2,5-difluoro-1,4-phenylene, $Z^3$ is a single bond or carbonyloxy.

Item 8 is the liquid crystal composition of any one of items 1 to 7 which includes at least one compound selected from the group of compounds represented by formulae (3-1) to (3-13) as the third component:

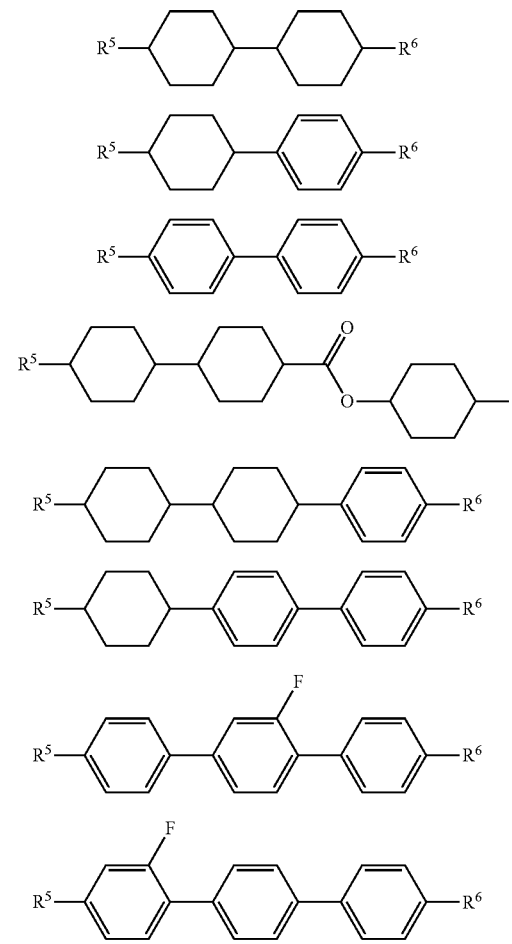

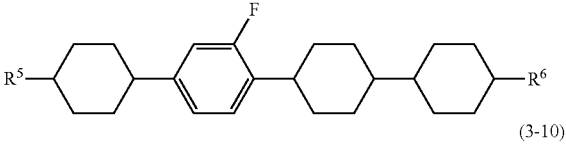

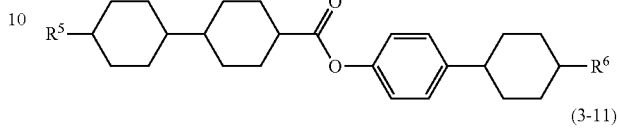

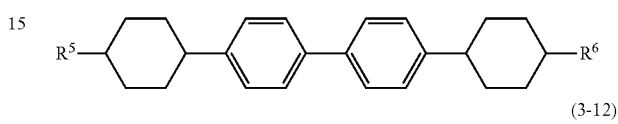

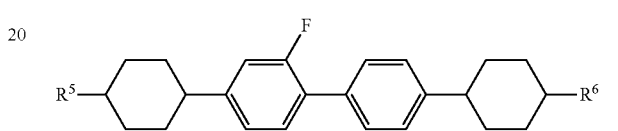

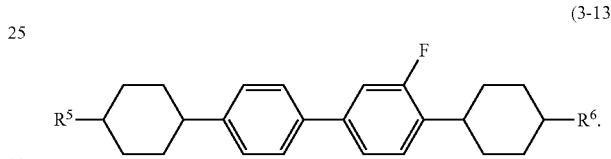

In formulae (3-1) to (3-13), $R^5$ and $R^6$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen.

Item 9 is the liquid crystal composition of item 7 or 8 in which the proportion of the third component is in the range of 20 wt % to 70 wt % based on the weight of the liquid crystal composition.

Item 10 is the liquid crystal composition of any one of items 1 to 9 which further includes at least one polymerizable compound selected from the group of compounds represented by formula (4) as an additive component:

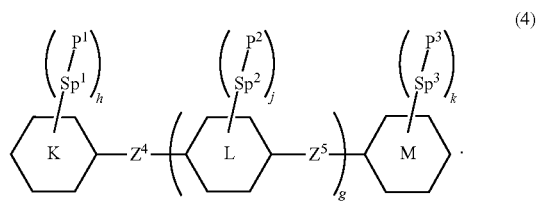

In formula (4), ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2, 3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; $Z^4$ and $Z^5$ are independently a single bond or alkylene having 1 to 10 carbons, and in the alkylene at least one —CH$_2$— may be replaced by —O—, —CO—, —COO— or —OCO—, at least one —CH$_2$—CH$_2$— may be replaced by —CH=CH—, —C(CH$_3$)=CH—, —CH=C(CH$_3$)— or —C(CH$_3$)=C(CH$_3$)—, and in these groups at least one hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one —CH$_2$— may be replaced by —O—, —COO—, —OCO— or —OCOO—, at least one —CH$_2$—CH$_2$— may be replaced by —CH=CH— or —C≡C—, and in these groups at least one hydrogen may be replaced by fluorine or chlorine; g is 0, 1 or 2; h, j and k are independently 0, 1, 2, 3 or 4; and the sum of h, j and k is 1 or more.

Item 11 is the liquid crystal composition of item 10 in which $P^1$, $P^2$ and $P^3$ in formula (4) are independently a polymerizable group selected from the group of groups represented by formulae (P-1) to (P-6):

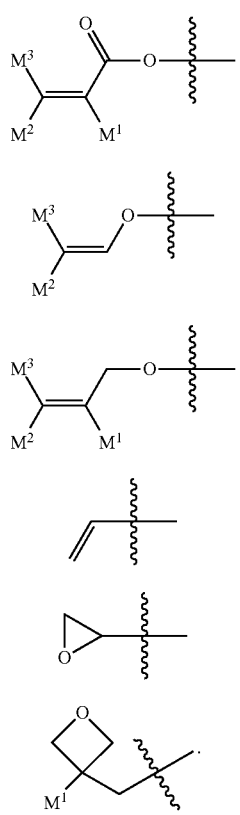

In formulae (P-1) to (P-6), $M^1$, $M^2$ and $M^3$ are independently hydrogen, fluorine, alkyl having 1 to 5 carbons, or alkyl having 1 to 5 carbons in which at least one hydrogen has been replaced by halogen.

In formula (4), when all of the h-numbering $P^1$ and the k-numbering $P^3$ are a group represented by formula (P-4), at least one of the h-numbering $Sp^1$ and the k-numbering $Sp^3$ is alkylene in which at least one —CH$_2$— has been replaced by —O—, —COO—, —OCO— or —OCOO—.

Item 12 is the liquid crystal composition of any one of items 1 to 11 which includes at least one polymerizable compound selected from the group of compounds represented by formulae (4-1) to (4-27) as the additive component:

(4-1)

(4-2)

(4-3)

(4-4)

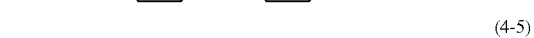
(4-5)

(4-6)

(4-7)

(4-8)

(4-9)

(4-10)

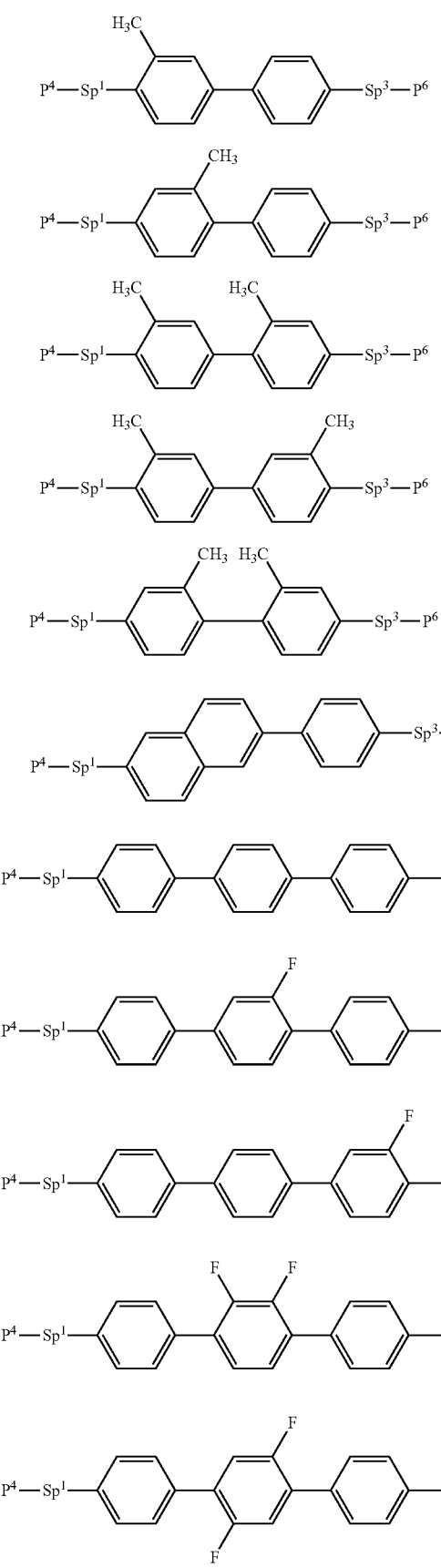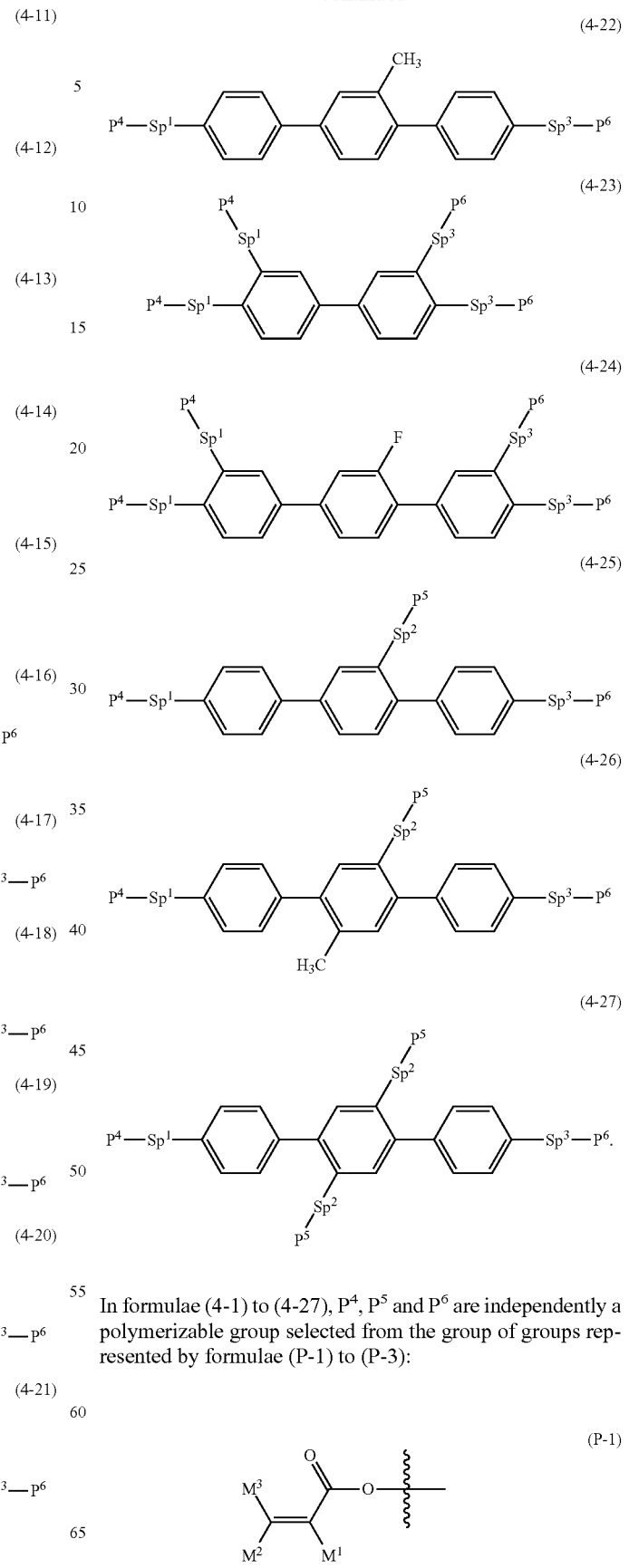
In formulae (4-1) to (4-27), $P^4$, $P^5$ and $P^6$ are independently a polymerizable group selected from the group of groups represented by formulae (P-1) to (P-3):

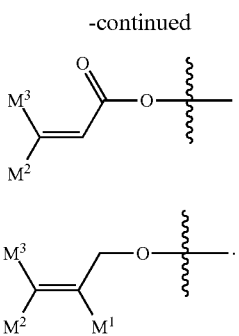

In formulae (P-1) to (P-3), $M^1$, $M^2$ and $M^3$ are independently hydrogen, fluorine, alkyl having 1 to 5 carbons, or alkyl having 1 to 5 carbons in which at least one hydrogen has been replaced by halogen.

In formulae (4-1) to (4-27), $Sp^1$, $Sp^2$ and $Sp^3$ are independently a single bond or alkylene having 1 to 10 carbons, and in the alkylene at least one —$CH_2$— may be replaced by —O—, —COO—, —OCO— or —OCOO—, at least one —$CH_2$—$CH_2$— may be replaced by —CH=CH— or —C≡C—, and in these groups at least one hydrogen may be replaced by fluorine or chlorine.

Item 13 is the liquid crystal composition of any one of items 10 to 12 in which the proportion of the additive component is in the range of 0.03 wt % to 10 wt % based on the weight of the liquid crystal composition.

Item 14 is an LCD device including the liquid crystal composition of any one of items 1 to 13.

Item 15 is the LCD device of item 14 of which the operating mode is an IPS mode, a VA mode, an FFS mode or an FPA mode, and the driving mode is an active matrix mode.

Item 16 is an LCD device of a polymer sustained alignment (PSA) type which includes the liquid crystal composition of any one of items 10 to 13, or includes the liquid crystal composition in which the polymerizable compound has been polymerized.

Item 17 is use of the liquid crystal composition of any one of items 1 to 13 for an LCD device.

Item 18 is use of the liquid crystal composition of any one of items 10 to 13 for an LCD device of a PSA type.

The invention further includes the following items: a) the composition described above which also including at least one of additives such as an optically active compound, an antioxidant, a UV light absorbent, a coloring matter, an antifoaming agent, a polymerizable compound, a polymerization initiator and a polymerization inhibitor; b) an AM device including the composition described above; c) the composition described above which further includes a polymerizable compound and a AM device of a PSA type including this composition; d) an AM device of a PSA type including the composition described above in which a polymerizable compound in this composition has been polymerized; e) a device including the composition described above and having a mode of PC, TN, STN, ECB, OCB, IPS, VA, FFS or FPA; f) a transmission-type device including the composition described above; g) use of the composition described above as a composition having a nematic phase; and h) use of the composition described above as an optically active composition by adding an optically active compound to the composition.

The composition of the invention will be described in the following order. First, the constitution of component compounds in the composition are described. Second, the main characteristics of the component compounds and the main effects of these compounds on the composition are described. Third, the combination of the components in the composition, desirable proportions of the components and their bases are described. Fourth, desirable embodiments of the component compounds are described. Fifth, desirable component compounds are shown. Sixth, additives that may be added to the composition are described. Seventh, methods for synthesizing the component compounds are described. Last, the application of the composition is described.

First, the constitution of component compounds in the composition are described. The compositions of the invention are classified into composition A and composition B. Composition A may further include other liquid crystal compound, an additive and so forth, in addition to liquid crystal compounds selected from compounds (1), (2) and (3). "Other liquid crystal compound" is a liquid crystal compound that is different from compounds (1), (2) and (3). Such a compound is mixed with the composition for further adjusting the characteristics. Examples of the additive include an optically active compound, an antioxidant, a UV light absorbent, a coloring matter, an antifoaming agent, a polymerizable compound, a polymerization initiator and a polymerization inhibitor.

Composition B consists essentially of liquid crystal compounds selected from compounds (1), (2) and (3). The term "essentially" means that the composition may include an additive, but does not include any other liquid crystal compound. Composition B has a smaller number of components than composition A. Composition B is preferred to composition A in view of cost reduction. Composition A is preferred to composition B in view of the fact that characteristics can be further adjusted by mixing with other liquid crystal compound.

Second, the main characteristics of the component compounds and the main effects of these compounds on the characteristics of the composition are described. The main characteristics of the component compounds are summarized in Table 2 on the basis of the effects of the invention. In Table 2, the symbol "L" stands for "large" or "high", "M" stands for "medium", and "S" stands for "small" or "low." The symbols "L," "M" and "S" mean a classification based on a qualitative comparison among the component compounds, and 0 (zero) means that the value is close to zero.

TABLE 2

Characteristics of Compounds

| | Compound | | |
| --- | --- | --- | --- |
| | Compound (1) | Compound (2) | Compound (3) |
| Maximum Temperature | M | S-L | S-L |
| Viscosity | M | M-L | S-M |
| Optical Anisotropy | L | M-L | S-L |
| Dielectric Anisotropy | 0 | M-L[1)] | 0 |
| Specific Resistance | L | L | L |

[1)]The value of the dielectric anisotropy is negative, and the symbol expresses the magnitude of the absolute value.

Main effects of the component compounds on characteristics of the composition upon mixing the component compounds with the composition are described as follows. Compound (1) increases the optical anisotropy. Compound (2) increases the dielectric anisotropy and decreases the minimum temperature. Compound (3) decreases the viscosity or increases the maximum temperature. Compound (4) gives a polymer by polymerization, and this polymer decreases the response time of a device, and reduces image burn-in.

Third, the combination of the components in the composition, desirable proportions of the same and their bases are described. A desirable combination of the components in the composition is the 1$^{st}$ and 2$^{nd}$ components, the 1$^{st}$ and 3$^{rd}$ components, the 1$^{st}$ and additive components, the 1$^{st}$, 2$^{nd}$ and 3$^{rd}$ components, the 1$^{st}$, 2$^{nd}$ and additive components, the 1$^{st}$, 3$^{rd}$ and additive components, or the 1$^{st}$, 2$^{nd}$, 3$^{rd}$ and additive components. A more desirable combination is the 1$^{st}$, 2$^{nd}$ and 3$^{rd}$ components, or the 1$^{st}$, 2$^{nd}$, 3$^{rd}$ and additive components.

A desirable proportion of the first component is about 3 wt % or more for increasing the maximum temperature, and about 20 wt % or less for decreasing the minimum temperature. A more desirable proportion is about 3 wt % to about 15 wt %. A particularly desirable proportion is about 5 wt % to about 15 wt %.

A desirable proportion of the second component is about 20 wt % or more for increasing the Δ∈, and about 70 wt % or less for decreasing the minimum temperature. A more desirable proportion is about 25 wt % to about 65 wt %. A particularly desirable proportion is about 30 wt % to about 60 wt %.

A desirable proportion of the third component is about 20 wt % or more for increasing the maximum temperature or for decreasing the viscosity, and about 70 wt % or less for increasing the Δ∈. A more desirable proportion is about 20 wt % to about 65 wt %. A particularly desirable proportion is about 25 wt % to about 60 wt %.

Compound (4) is added to the composition for adapting to a device of a PSA type. A desirable proportion of the additive is about 0.03 wt % or more for orienting liquid crystal molecules, and about 10 wt % or less for preventing display defects of a device. A more desirable proportion is about 0.1 wt % to about 2 wt %. A particularly desirable proportion is about 0.2 wt % to about 1 wt %.

Fourth, desirable embodiments of the component compounds are described. In formulae (1), (2) and (3), $R^1$, $R^2$, $R^5$ and $R^6$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen. Desirable $R^1$, $R^2$, $R^5$ or $R^6$ are alkenyl having 2 to 12 carbons for decreasing the viscosity, or are alkyl having 1 to 12 carbons for increasing the stability. $R^3$ and $R^4$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen has been replaced by halogen. Desirable $R^3$ or $R^4$ is alkyl having 1 to 12 carbons for increasing the stability, or is alkoxy having 1 to 12 carbons for increasing the dielectric anisotropy.

The alkyl is straight or branched, and does not include cycloalkyl. Straight alkyl is preferred to branched alkyl. This rule applies to a terminal group such as alkoxy or alkenyl. Halogen means fluorine, chlorine, bromine or iodine. Desirable halogen is fluorine or chlorine. More desirable halogen is fluorine.

Desirable alkyl is methyl, ethyl, propyl, butyl, pentyl, hexyl, heptyl or octyl. More desirable alkyl is ethyl, propyl, butyl, pentyl or heptyl for decreasing the viscosity.

Desirable alkoxy is methoxy, ethoxy, propoxy, butoxy, pentyloxy, hexyloxy or heptyloxy. More desirable alkoxy is methoxy or ethoxy for decreasing the viscosity.

Desirable alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. More desirable alkenyl is vinyl, 1-propenyl, 3-butenyl or 3-pentenyl for decreasing the viscosity. The desirable configuration of —CH═CH— in the alkenyl depends on the position of the double bond. Trans is preferable for alkenyl groups such as 1-propenyl, 1-butenyl, 1-pentenyl, 1-hexenyl, 3-pentenyl and 3-hexenyl for decreasing the viscosity. Cis is preferable for alkenyl groups such as 2-butenyl, 2-pentenyl and 2-hexenyl.

Desirable alkenyloxy is vinyloxy, allyloxy, 3-butenyloxy, 3-pentenyloxy or 4-pentenyloxy. More desirable alkenyloxy is allyloxy or 3-butenyloxy for decreasing the viscosity.

Desirable examples of alkyl in which at least one hydrogen has been replaced by halogen are fluoromethyl, 2-fluoroethyl, 3-propyl, 4-fluorobutyl, 5-fluoropentyl, 6-fluorohexyl, 7-fluoroheptyl and 8-fluorooctyl. More desirable alkyl is 2-fluoroethyl, 3-propyl, 4-fluorobutyl or 5-fluoropentyl for increasing the dielectric anisotropy.

Desirable examples of alkenyl in which at least one hydrogen has been replaced by halogen are 2,2-difluorovinyl, 3,3-difluoro-2-propenyl, 4,4-difluoro-3-butenyl, 5,5-difluoro-4-pentenyl and 6,6-difluoro-5-hexenyl. More desirable examples are 2,2-difluorovinyl and 4,4-difluoro-3-butenyl for decreasing the viscosity.

Ring A, ring B and ring C are independently 1,4-phenylene, or 1,4-phenylene in which at least one hydrogen has been replaced by fluorine or chlorine. Desirable ring A, ring B or ring C is 1,4-phenylene for decreasing the viscosity. Ring D and ring F are independently 1,4-cyclohexylene, 1,4-cyclohexenylene, 1,4-phenylene, 1,4-phenylene in which at least one hydrogen has been replaced by fluorine or chlorine, or tetrahydropyran-2,5-diyl. Desirable example of "1,4-phenylene in which at least one hydrogen has been replaced by fluorine or chlorine" is 2-fluoro-1,4-phenylene, 2,3-difluoro-1,4-phenylene and 2-chloro-3-fluoro-1,4-phenylene. Desirable ring D or ring F is 1,4-cyclohexylene for decreasing the viscosity, or is tetrahydropyran-2,5-diyl for increasing the dielectric anisotropy, or is 1,4-phenylene for increasing the optical anisotropy. Regarding the configuration of 1,4-cyclohexylene, trans is preferred to cis for increasing the maximum temperature. Tetrahydropyran-2,5-diyl may be

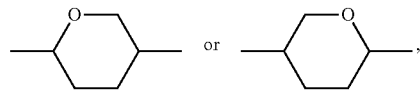

and is preferably

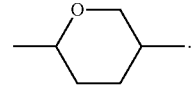

Ring E is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Desirable ring E is 2,3-difluoro-1,4-phenylene for decreasing the viscosity, or is 2-chloro-3-fluoro-1,4-phenylene for decreasing the optical anisotropy, or is 7,8-difluorochroman-2,6-diyl for increasing the dielectric anisotropy.

Ring G and ring J are independently 1,4-cyclohexylene, 1,4-phenylene, 2-fluoro-1,4-phenylene or 2,5-difluoro-1,4-phenylene. Desirable ring G or ring J is 1,4-cyclohexylene for decreasing the viscosity or for increasing the maximum temperature, or is 1,4-phenylene for decreasing the minimum temperature.

$Z^1$ and $Z^2$ are independently a single bond, ethylene, carbonyloxy or methyleneoxy. Desirable $Z^1$ or $Z^2$ is a single bond for decreasing the viscosity, or is ethylene for decreasing the minimum temperature, or is methyleneoxy for increasing the dielectric anisotropy. $Z^3$ is a single bond, ethylene or carbonyloxy. Desirable $Z^3$ is a single bond for increasing the stability.

a is 1, 2 or 3, b is 0 or 1, and the sum of a and b is 3 or less. Desirable a is 1 for decreasing the viscosity, or is 2 or 3 for increasing the maximum temperature. Desirable b is 0 for decreasing the viscosity, or is 1 for decreasing the minimum temperature. n is 1, 2 or 3. Desirable n is 1 for decreasing the viscosity, or is 2 or 3 for increasing the maximum temperature.

In formula (2), $Z^1$ and $Z^2$ are independently a single bond, carbonyloxy or methyleneoxy, and when the sum of a and b is 2, and the a-numbering ring D and the b-numbering ring F are 1,4-phenylene or 1,4-phenylene in which at least one hydrogen has been replaced by fluorine or chlorine, $Z^1$ or $Z^2$ is not ethylene.

In formula (3), $Z^3$ is a single bond or carbonyloxy, and when n is 2 and two of rings G and ring J are 1,4-phenylene, 2-fluoro-1,4-phenylene or 2,5-difluoro-1,4-phenylene, $Z^3$ is not ethylene.

In formula (4), $P^1$, $P^2$ and $P^3$ are independently a polymerizable group. Desirable $P^1$, $P^2$ or $P^3$ is a polymerizable group selected from the group of groups represented by formulae (P-1) to (P-6). More desirable $P^1$, $P^2$ or $P^3$ is group (P-1) or group (P-2). Particularly desirable group (P-1) is —OCO—CH=CH$_2$ or —OCO—C(CH$_3$)=CH$_2$. A wavy line in groups (P-1) to (P-6) indicates the binding site.

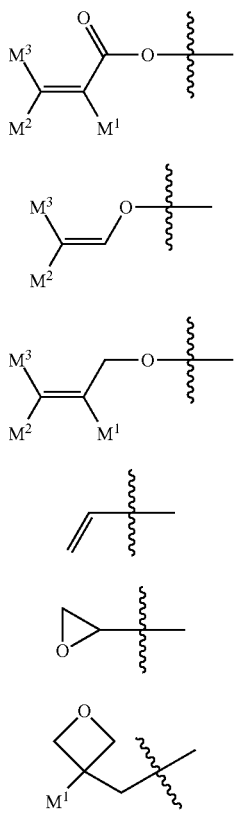

In groups (P-1) to (P-6), $M^1$, $M^2$ and $M^3$ are independently hydrogen, fluorine, alkyl having 1 to 5 carbons, or alkyl having 1 to 5 carbons in which at least one hydrogen has been replaced by halogen. Desirable $M^1$, $M^2$ or $M^3$ is hydrogen or methyl for increasing the reactivity. More desirable $M^1$ is methyl, and more desirable $M^2$ or $M^3$ is hydrogen. In group (4), arbitrary two of $M^1$, $M^2$ or $M^3$ in $P^1$, $P^2$ and $P^3$ may be the same or different when at least two of the h-numbering $P^1$, the j-numbering $P^2$ and the k-numbering $P^3$ are group (P-1). The same rule applies to group (P-2) or (P-3).

When all of the h-numbering $P^1$ and the k-numbering $P^3$ are group (P-4), at least one of the h-numbering $Sp^1$ and the k-numbering $Sp^3$ is alkylene in which at least one —CH$_2$— has been replaced by —O—, —COO—, —OCO— or —OCOO—. That is to say, all of the h-numbering $P^1$ and the k-numbering $P^3$ should not be alkenyl such as 1-propenyl.

In formulae (4-1) to (4-27), $P^4$, $P^5$ and $P^6$ are independently a group selected from groups represented by formulae (P-1) to (P-3). Desirable $P^4$, $P^5$ or $P^6$ is group (P-1) or group (P-2). More desirable group (P-1) is —OCO—CH=CH$_2$ or —OCO—C(CH$_3$)=CH$_2$. A wavy line in groups (P-1) to (P-3) indicates the binding site.

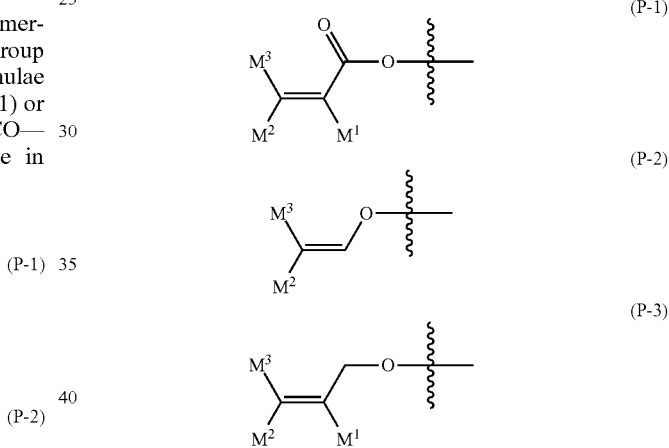

Arbitrary two $M^1$, $M^2$ or $M^3$ in $P^4$, $P^5$ and $P^6$ may be the same or different when at least two of one or two $P^4$, one or two $P^5$, and one or two $P^6$ are group (P-1). The same rule applies to group (P-2) or group (P-3).

In formula (4), $Sp^1$, $Sp^2$ and $Sp^3$ are independently a single bond or alkylene having 1 to 10 carbons, and in the alkylene at least one —CH$_2$— may be replaced by —O—, —COO—, —OCO— or —OCOO—, at least one —CH$_2$—CH$_2$— may be replaced by —CH=CH— or —C≡C—, and in these groups at least one hydrogen may be replaced by fluorine or chlorine. Desirable $Sp^1$, $Sp^2$ or $Sp^3$ is a single bond.

Ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen. Desirable ring K or ring M is phenyl. Ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine- 2,5-diyl or pyridine-2,5-diyl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen. Desirable ring L is 1,4-phenylene or 2-fluoro-1,4-phenylene.

$Z^4$ and $Z^5$ are independently a single bond or alkylene having 1 to 10 carbons, and in the alkylene at least one —$CH_2$— may be replaced by —O—, —CO—, —COO— or —OCO—, at least one —$CH_2$—$CH_2$— may be replaced by —CH=CH—, —C($CH_3$)=CH—, —CH=C($CH_3$)— or —C($CH_3$)=C($CH_3$)—, and in these groups at least one hydrogen may be replaced by fluorine or chlorine. Desirable $Z^4$ or $Z^5$ is a single bond, —$CH_2CH_2$—, —$CH_2O$—, —$OCH_2$—, —COO— or —OCO—. More desirable $Z^4$ or $Z^5$ is a single bond.

g is 0, 1 or 2. Desirable g is 0 or 1. h, j and k are independently 0, 1, 2, 3 or 4, and the sum of h, j and k is 1 or more. Desirable h, j or k is 1 or 2.

Fifth, desirable component compounds are shown. Desirable compounds (1) are compounds (1-1) to (1-4) of item 2. It is desirable that at least one compound in the first component should be compound (1-1) among these compounds.

Desirable compounds (2) are compounds (2-1) to (2-19) of item 5. It is desirable that at least one compound in the second component is compound (2-1), (2-2), (2-3), (2-4), (2-6), (2-7), (2-8), (2-9) or (2-13) among these compounds. It is desirable that at least two compounds in the second component are a combination of compounds (2-1) and (2-6), compounds (2-1) and (2-13), compounds (2-2) and (2-7), compounds (2-3) and (2-6), compounds (2-3) and (2-8), compounds (2-4) and (2-6), or compounds (2-4) and (2-8).

Desirable compounds (3) are compounds (3-1) to (3-13) of item 8. It is desirable that at least one compound in the third component is compound (3-1), (3-3), (3-5), (3-6) or (3-7) among these compounds. It is desirable that at least two compounds in the third component are a combination of compounds (3-1) and (3-3), or compounds (3-1) and (3-5).

Desirable compounds (4) are compounds (4-1) to (4-27) of item 12. It is desirable that at least one compound in the additive component is compound (4-1), (4-2), (4-24), (4-25), (4-26) or (4-27) among these compounds. It is desirable that at least two compounds in the additive component are a combination of compounds (4-1) and (4-2), compounds (4-1) and (4-18), compounds (4-2) and (4-24), compounds (4-2) and (4-25), compounds (4-2) and (4-26), compounds (4-25) and (4-26), or compounds (4-18) and (4-24). In groups (P-1) to (P-3), Desirable $M^1$, $M^2$ or $M^3$ is hydrogen or methyl. Desirable $Sp^1$, $Sp^2$ or $Sp^3$ is a single bond, —$CH_2CH_2$—, —$CH_2O$—, —$OCH_2$—, —COO—, —OCO—, —CO—CH=CH— or —CH=CH—CO—.

Sixth, additives that may be added to the composition are described. Such additives include an optically active compound, an antioxidant, a UV light absorbent, a coloring matter, an antifoaming agent, a polymerizable compound, a polymerization initiator and a polymerization inhibitor. The optically active compound is added to the composition for inducing the helical structure of liquid crystal molecules and giving a twist angle, and examples thereof include compounds (5-1) to (5-5). A desirable proportion of the optically active compound is about 5 wt % or less, and a more desirable proportion is about 0.01 wt % to about 2 wt %.

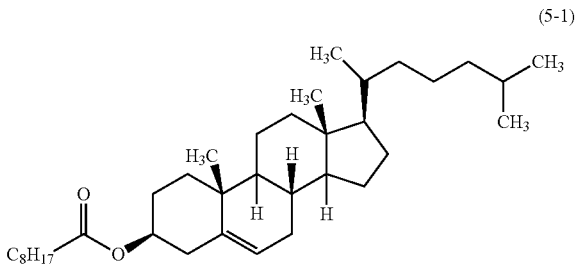

(5-1)

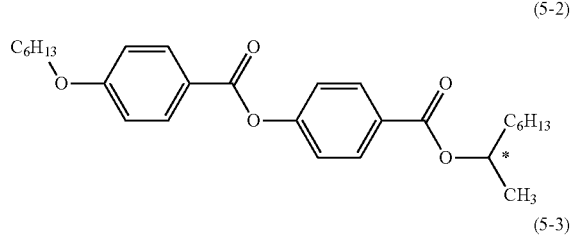

(5-2)

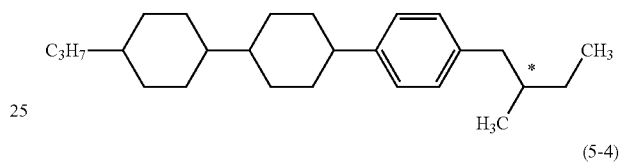

(5-3)

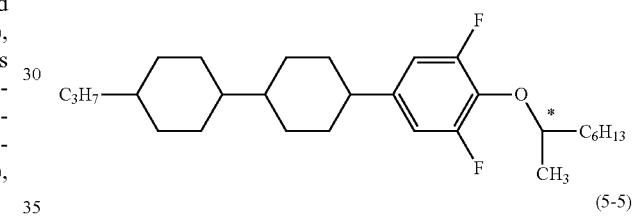

(5-4)

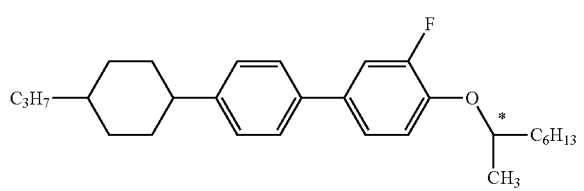

(5-5)

The antioxidant is added to the composition in order to prevent a decrease in specific resistance that is caused by heating under air, or to maintain a large voltage holding ratio at a temperature close to the maximum temperature as well as at room temperature, after the device has been used for a long period of time. A desirable example of the antioxidant is compound (6) where n is an integer of from 1 to 9, for instance.

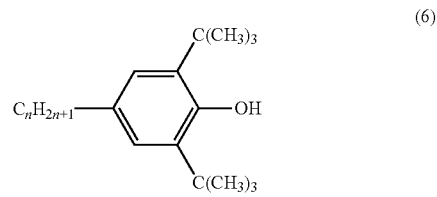

(6)

In compound (6), desirable n is 1, 3, 5, 7 or 9, and more desirable n is 7. Compound (6) of n=7 is effective in maintaining a large voltage holding ratio at a temperature close to the maximum temperature as well as at room temperature after the device has been used for long time, as having a low volatility. A desirable proportion of the antioxidant is about 50 ppm or more for achieving its effect, and is about 600 ppm or less for avoiding a decrease in the maximum temperature or avoiding an increase in the minimum temperature. A more desirable proportion is in the range of about 100 ppm to about 300 ppm.

Desirable examples of the UV light absorbent include benzophenone derivatives, benzoate derivatives and triazole derivatives. A light stabilizer such as an amine having steric hindrance is also desirable. A desirable proportion of the UV light absorbent or the light stabilizer is about 50 ppm or more for achieving its effect, and is about 10,000 ppm or less for avoiding a decrease in the maximum temperature or avoiding an increase in the minimum temperature. A more desirable proportion is in the range of about 100 ppm to about 10,000 ppm.

A dichroic dye such as an azo dye or an anthraquinone dye is added to the composition for adapting to a device of a guest host (GH) mode. A desirable proportion of the coloring matter is in the range of about 0.01 wt % to about 10 wt %. The antifoaming agent such as dimethyl silicone oil or methyl phenyl silicone oil is added to the composition for preventing foam formation. A desirable proportion of the antifoaming agent is about 1 ppm or more for achieving its effect, and is about 1,000 ppm or less for avoiding a poor display. A more desirable proportion is in the range of about 1 ppm to about 500 ppm.

The polymerizable compound is used for adapting to a device of a PSA mode. Compound (4) is suitable for this. A polymerizable compound different from compound (4) may be added to the composition, together with compound (4). Desired examples of the polymerizable compound include compounds such as acrylates, methacrylates, vinyl compounds, vinyloxy compounds, propenyl ethers, epoxy compounds (oxiranes, oxetanes) and vinyl ketones. More desirable examples are acrylate derivatives and methacrylate derivatives. A desirable proportion of compound (4) is 10 wt % or more based on the total weight of the polymerizable compound. A more desirable proportion is 50 wt % or more. An especially desirable ratio is 80 wt % or more. The even more desirable proportion is 100 wt %.

A polymerizable compound such as compound (4) is polymerized on irradiation with UV light. It may be polymerized in the presence of an initiator such as a photo-polymerization initiator. Suitable conditions for polymerization, and a suitable type and amount of the initiator are known to a person of ordinary skill in the art, and are described in the literature. For example, Irgacure 651™ (BASF), Irgacure 184™ (BASF) or Darocure 1173™ (BASF), each of which is a photo-initiator, is suitable for radical polymerization. A desirable proportion of the photo-polymerization initiator is in the range of about 0.1 wt % to about 5 wt % based on the weight of the polymerizable compound. A more desirable proportion is in the range of about 1 wt % to about 3 wt %.

A polymerization inhibitor may be added in order to prevent polymerization when a polymerizable compound such as compound (4) is kept in storage. The polymerizable compound is usually added to the composition without removing the polymerization inhibitor. Examples of the polymerization inhibitor include hydroquinone derivatives such as hydroquinone and methylhydroquinone, 4-tert-butylcatechol, 4-methoxyphenol and phenothiazine.

Seventh, methods for synthesizing the component compounds are described. These compounds can be synthesized by known methods, as exemplified below. Compound (1) may be prepared by the method described in JP H03-503651 A (1991). Compound (2-6) may be prepared by the method described in JP 2000-53602 A. Compound (3-1) may be prepared by the method described in JP S59-176221 A (1984). A compound of formula (6) of n=1 is available from Sigma-Aldrich Corporation. Compound (6) of n=7, for instance, may be synthesized with the method described in U.S. Pat. No. 3,660,505.

Compounds whose synthetic methods are not described above can be prepared with the methods described in books such as "Organic Syntheses" (John Wiley & Sons, Inc.), "Organic Reactions" (John Wiley & Sons, Inc.), "Comprehensive Organic Synthesis" (Pergamon Press), and "New experimental Chemistry Course" (Maruzen Co., Ltd., Japan). The composition is prepared with known methods using the compounds thus obtained. For example, the component compounds are mixed and dissolved in each other by heating.

Last, the application of the composition is described. The composition of the invention mainly has a minimum temperature of about −10° C. or lower, a maximum temperature of about 70° C. or higher, and an optical anisotropy in the range of about 0.07 to about 0.20. A composition having an optical anisotropy in the range of about 0.08 to about 0.25 may be prepared by adjusting the proportions of the component compounds or by mixing with other liquid crystal compound. Further, a composition having an optical anisotropy in the range of about 0.10 to about 0.30 may be prepared by this method. A device including this composition has a large voltage holding ratio. This composition is suitable for an AM device, especially for an AM device of a transmission type. This composition can be used as a composition having a nematic phase, and as an optically active composition by adding an optically active compound.

The composition can be used for an AM device, and can also be used for a PM device. The composition can also be used for an AM device or a PM device having a mode such as PC, TN, STN, ECB, OCB, IPS, FFS, VA and FPA. It is particularly desirable to use the composition for an AM device of a mode of TN, OCB, IPS or FFS. In an AM device of an IPS or FFS mode, the orientation of liquid crystal molecules may be parallel or perpendicular to the glass substrate, when no voltage is applied. These devices may be of a reflection type, a transmission type or a semi-transmission type. It is desirable to use the composition for a transmission-type device. The composition can be used for an amorphous silicon-TFT device or a polycrystal silicon-TFT device. The composition is also usable for an NCAP (nematic curvilinear aligned phase) device prepared by micro-capsulating the composition, and for a PD (polymer dispersed) device in which a 3D network-polymer is formed in the composition.

EXAMPLES

The invention will be described in more details by way of examples, but is not limited to the examples. For example, the invention includes a mixture of the composition of Example 1 and the composition of Example 2, and also includes a mixture prepared by mixing at least two of the compositions disclosed in Examples. The compounds prepared herein were identified by methods such as NMR analysis. The characteristics of the compounds, compositions and devices were measured with the methods described below.

NMR Analysis

A model DRX-500 apparatus made by Bruker BioSpin Corporation was used for the measurement. In the measurement of $^1$H-NMR, a sample was dissolved in a deuterated solvent such as $CDCl_3$, and the measurement was carried out under the conditions of room temperature, 500 MHz and an accumulation of 16 scans. Tetramethylsilane was used as an internal standard. In the measurement of $^{19}$F-NMR, CFCl$_3$ was used as an internal standard, and 24 scans were accumulated. In the explanation of the NMR spectra, the symbols s, d, t, q, quin, sex, m and br stand for a singlet, a doublet, a triplet, a quartet, a quintet, a sextet, a multiplet and a broad peak, respectively.

Gas Chromatographic Analysis:

A gas chromatograph Model GC-14B made by Shimadzu Corporation was used for the measurement. The carrier gas was helium (2 mL/min). The sample injector and the detector (FID) were set to 280° C. and 300° C., respectively. A capillary column DB-1 (length: 30 m, bore: 0.32 mm, film thickness: 0.25 μm; dimethylpolysiloxane as the stationary phase, non-polar) made by Agilent Technologies, Inc. was used to separate component compounds. After the column had been kept at 200° C. for 2 min, it was further heated to 280° C. at a rate of 5° C./min. A sample was dissolved in acetone (0.1 wt %), and 1 μL of the solution was injected into the sample injector. The recorder used was C-R5A Chromatopac Integrator from Shimadzu Corporation or its equivalent. The resulting gas chromatogram showed retention times of peaks and peak areas corresponding to the compounds.

A solvent, such as chloroform or hexane, etc., may also be used to dilute the sample. The following capillary columns may also be used to separate the component compounds: HP-1 made by Agilent Technologies Inc. (length: 30 m, bore: 0.32 mm, film thickness: 0.25 m), Rtx-1 made by Restek Corporation (length: 30 m, bore: 0.32 mm, film thickness: 0.25 μm), and BP-1 made by SGE International Pty. Ltd. (length: 30 m, bore: 0.32 mm, film thickness: 0.25 μm). A capillary column CBP1-M50-025 (length: 50 m, bore: 0.25 mm, film thickness: 0.25 μm) made by Shimadzu Corporation may also be used for avoiding an overlap of peaks of the compounds.

The proportions of the liquid crystal compounds included in the composition may be calculated with the following method. A mixture of the liquid crystal compounds are detected using a gas chromatograph (FID). The ratio of peak areas in the gas chromatogram corresponds to the ratio (weight ratio) of the liquid crystal compounds. When the capillary columns described above are used, the correction coefficient of respective liquid crystal compounds may be regarded as 1 (one). Accordingly, the proportions (in weight percent) of the liquid crystal compounds can be calculated from the ratio of peak areas.

Samples for Measurement

A composition itself was used as a sample when characteristics of the composition or device were measured. When characteristics of a compound were to be measured, a sample for measurement was prepared by mixing this compound (15 wt %) with a mother liquid crystal (85 wt %). The characteristic values of the compound were calculated from the values obtained from the measurements by an extrapolation method: (Extrapolated value)=(Measured value of sample)−0.85× (Measured value of mother liquid crystals)/0.15. When a smectic phase (or crystals) deposited at 25° C. at this ratio, the ratio of the compound to the mother liquid crystal was changed in the order of (10 wt %: 90 wt %), (5 wt %: 95 wt %) and (1 wt %: 99 wt %). The values of the maximum temperature, Δn, viscosity and Δ∈ of the compound were obtained by means of this extrapolation method.

The mother liquid crystal shown below was used. Proportions of the component compounds were expressed in terms of weight percent.

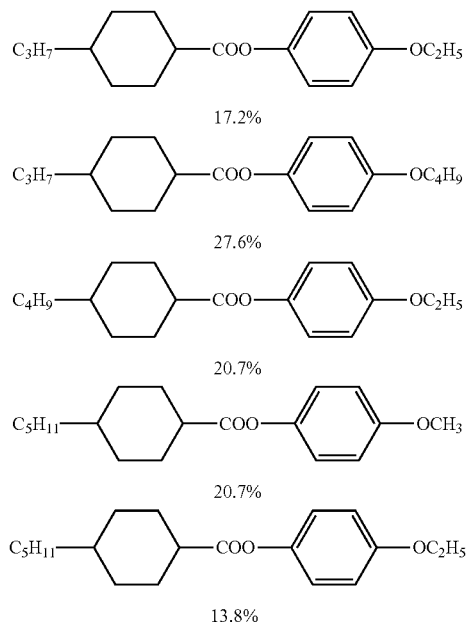

Measurement Methods

Characteristics of compounds were measured with the following methods. Most of them are applied as described in the standard "JEITA-ED-2521B" which was deliberated and established by Japan Electronics and Information Technology Industries Association (abbreviated to "JEITA"), or as modified thereon. No thin film transistor (TFT) was attached to the TN device used for measurement.

1) Maximum Temperature of a Nematic Phase (NI; ° C.):

A sample was placed on a hot plate in a melting point apparatus equipped with a polarizing microscope and was heated at the rate of 1° C./min. The temperature at which a part of the sample began to change from a nematic phase to an isotropic liquid was measured. The higher limit of the temperature range of a nematic phase may be abbreviated to "the maximum temperature."

2) Minimum Temperature of a Nematic Phase (Tc; ° C.):

A sample having a nematic phase was placed in glass vials and then kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc was expressed as "<−20° C." The lower limit of the temperature range of a nematic phase may be abbreviated to "the minimum temperature."

3) Viscosity (Bulk Viscosity; η; Measured at 20° C.; mPa·s):

An E-type viscometer from Tokyo Keiki Inc. was used for measurement.

4) Viscosity (Rotational Viscosity; γ1; Measured at 25° C.; mpa·s):

The measurement was carried out with the method described in M. Imai, et al., *Molecular Crystals and Liquid Crystals*, Vol. 259, p, 37 (1995). A sample was poured into a VA device in which the distance between the two glass substrates (cell gap) was 20 m. A voltage in the range of 39 V to 50 V was applied stepwise with an increment of 1 volt to this device. After a period of 0.2 sec with no voltage, a voltage was applied repeatedly under the conditions of only one rectangular wave (rectangular pulse; 0.2 sec) and no voltage (2 sec).

The peak current and the peak time of the transient current generated by the applied voltage were measured. The value of rotational viscosity was obtained from these measured values and Equation (8) on page 40 of the paper presented by M. Imai, et al. The value of the dielectric anisotropy necessary for the present calculation was measured according to item 6).

5) Optical Anisotropy (Refractive Index Anisotropy; Δn; Measured at 25° C.):

The measurement was carried out using an Abbe refractometer with a polarizing plate attached to the ocular, using light at a wavelength of 589 nm. The surface of the main prism was rubbed in one direction, and then a sample was placed on the main prism. The refractive index $n_∥$ was measured when the direction of the polarized light was parallel to that of rubbing. The refractive index $n_⊥$ was measured when the direction of polarized light was perpendicular to that of rubbing. The value of the optical anisotropy (Δn) was calculated using the equation "$Δn=n_∥−n_⊥$."

6) Dielectric Anisotropy (Δ∈; Measured at 25° C.):

The value of dielectric anisotropy was calculated from the equation "$Δ∈=∈_∥−E_⊥$." Dielectric constants ($∈_∥$ and $E_⊥$) were measured as follows.

1) Measurement of $Δ_∥$: A solution of octadecyltriethoxysilane (0.16 mL) in ethanol (20 mL) was applied to fully cleaned glass substrates. The glass substrates were rotated with a spinner, and then heated at 150° C. for one hour. A sample was poured in a VA device in which the distance between the two glass substrates (cell gap) was 4 μm, and then this device was sealed with a UV-curable adhesive. Sine waves (0.5 V, 1 kHz) were applied to this device, and the dielectric constant $∈_∥$ in the major axis direction of liquid crystal molecules was measured after 2 sec.

2) Measurement of $∈_⊥$: A polyimide solution was applied to fully cleaned glass substrates. The glass substrates were calcined, and then the resulting alignment film was subjected to rubbing. A sample was poured into a TN device in which the distance between the two glass substrates (cell gap) was 9 m and the twist angle was 80°. Sine waves (0.5 V, 1 kHz) were applied to this device, and the dielectric constant $∈_⊥$ in the minor axis direction of liquid crystal molecules was measured after 2 sec.

7) Threshold Voltage (Vth; Measured at 25° C.; V):

An LCD evaluation system Model LCD-5100 made by Otsuka Electronics Co., Ltd. was used for the measurement. The light source was a halogen lamp. A sample was poured into a VA device having a normally black mode, in which the distance between the two glass substrates (cell gap) was 4 μm and the rubbing direction was antiparallel, and then this device was sealed with a UV-curable adhesive. The voltage to be applied to this device (60 Hz, rectangular waves) was stepwise increased in 0.02 V increments from 0 V up to 20 V. During the increase, the device was irradiated perpendicularly with light, and the amount of light passing through the device was measured. A voltage-transmittance curve was prepared, in which the maximum amount of light corresponded to 100% transmittance and the minimum amount of light corresponded to 0% transmittance. The threshold voltage was defined as the voltage at 10% transmittance.

8) Voltage Holding Ratio (VHR-1; Measured at 25° C.; %):

A TN device used for the measurement had a polyimide alignment film, and a distance (cell gap) of 5 μm between two glass substrates. A sample was poured into the device, and then this TN device was sealed with a UV-curable adhesive. A pulse voltage (60 μs at 5 V) was applied to this device to charge the device. The decaying voltage was measured for 16.7 milliseconds with a high-speed voltmeter, and area A between the voltage curve and the horizontal axis in a unit cycle was obtained. The voltage holding ratio was defined as the percentage of area A to area B that was the area without decay.

9) Voltage Holding Ratio (VHR-2; Measured at 80° C.; %):

A voltage holding ratio was measured by the method described above, except that it was measured at 80° C. instead of 25° C. The results were shown with the symbol "VHR-2."

10) Voltage Holding Ratio (VHR-3; Measured at 25° C.; %):

The stability to UV light was evaluated by measuring a voltage holding ratio after UV-irradiation. A TN device used for the measurement had a polyimide alignment film and a cell gap of 5 μm. A sample was poured into this device, and then the device was irradiated with light for 20 min. The light source was an ultra-high-pressure mercury lamp USH-500D (made by Ushio, Inc.), and the distance between the device and the light source was 20 cm. In measuring VHR-3, the decaying voltage was measured for 16.7 milliseconds. A composition having a large VHR-3 has a high stability to UV light. The value of VHR-3 is preferably 90% or more, and more preferably 95% or more.

11) Voltage Holding Ratio (VHR-4; Measured at 25° C.; %):

A TN device into which a sample was poured was heated in a constant-temperature bath at 80° C. for 500 hours, and then the stability to heat was evaluated by measuring the voltage holding ratio. In measuring VHR-4, the decreasing voltage was measured for 16.7 milliseconds. A composition having a large VHR-4 has a high stability to heat.

12) Response Time (τ; Measured at 25° C.; Millisecond):

The measurement was carried out with an LCD evaluation system Model LCD-5100 made by Otsuka Electronics Co., Ltd. The light source was a halogen lamp. The low-pass filter was set at 5 kHz. A sample was poured in a VA device having a normally black mode, in which the cell gap between the two glass substrates was 4 μm and the rubbing direction was antiparallel, and then the device was sealed with a UV-curable adhesive. Rectangular waves (60 Hz, 10V, 0.5 sec) were applied to the device while the device was irradiated perpendicularly with light, and the amount of the light passing the device was measured. The maximum amount of light corresponded to 100% transmittance, and the minimum amount of light corresponded to 0% transmittance. The response time was the period of time required for a change from 90% to 10% transmittance (fall time; millisecond).

13) Specific Resistance (ρ; Measured at 25° C.; Ω·cm):

A sample of 1.0 mL was poured into a vessel equipped with electrodes. A DC voltage (10 V) was applied to the vessel, and the DC current was measured after 10 sec. The specific resistance p was calculated with the equation "ρ=[(voltage)×(electric capacity of vessel)]/[(DC current)×(dielectric constant in vacuum)]."

The compounds described in Examples were expressed in terms of symbols according to the definition in Table 3 below. In Table 3, the configuration of 1,4-cyclohexylene is trans. The parenthesized number next to a symbolized compound in any Example corresponds to the number of the compound. The symbol "(-)" means any other liquid crystal compound. The proportion (percentage) of a liquid crystal compound means the weight percentages (wt %) based on the weight of the liquid crystal composition. Last, the values of characteristics of the composition are summarized.

TABLE 3

Method of expressing compounds using symbols
R—(A₁)—Z₁— ... —Zₙ—(Aₙ)—R'

| 1) Left-terminal Group R— | Symbol |
|---|---|
| FC$_n$H$_{2n}$— | Fn— |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| CH$_2$=CHCOO— | AC— |
| CH$_2$=C(CH$_3$)COO— | MAC— |

| 2) Right-terminal Group —R' | Symbol |
|---|---|
| —C$_n$H$_{2n+1}$ | -n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —OCOCH=CH$_2$ | —AC |
| —OCOC(CH$_3$)=CH$_2$ | —MAC |

| 3) Bonding Group —Z$_n$— | Symbol |
|---|---|
| —C$_n$H$_{2n}$— | n |
| —COO— | E |
| —CH=CH— | V |
| —CH=CHO— | VO |
| —OCH=CH— | OV |
| —CH$_2$O— | 1O |
| —OCH$_2$— | O1 |

| 4) Ring Structure —A$_n$— | Symbol |
|---|---|
|  | H |
| 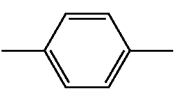 | B |
| 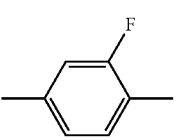 | B(F) |
| 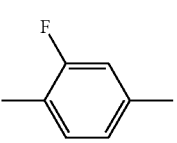 | B(2F) |
| 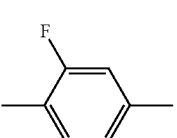 | B(2F,5F) |
|  | B(2F,3F) |
| 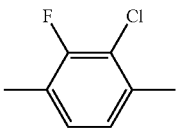 | B(2F,3Cl) |
| 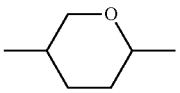 | dh |
| 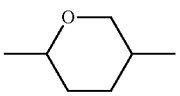 | Dh |
| 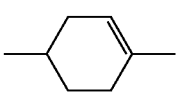 | ch |
| 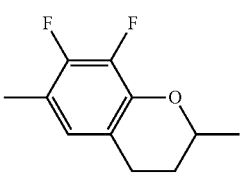 | Cro(7F,8F) |

5) Examples of Description

Example 1. 1-B2BB-2V

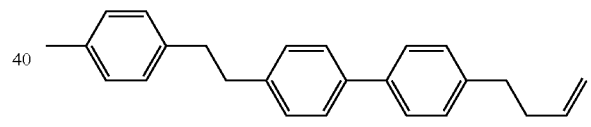

Example 2. 3-HB(2F,3F)—O2

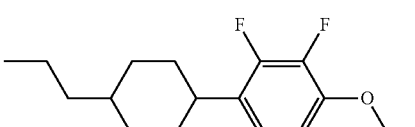

Example 3. 3-HHB-1

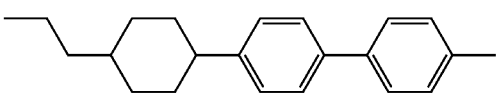

Example 4. AC—BB—AC

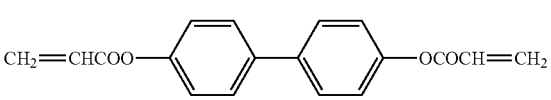

| | | |
|---|---|---|
| 1-B2BB-2V | (1-1) | 8% |
| 3-BB(2F,3F)-O2 | (2-4) | 12% |
| 5-BB(2F,3F)-O2 | (2-4) | 8% |

| 2-HH1OB(2F,3F)-O2 | (2-8) | 10% |
| --- | --- | --- |
| 3-HH1OB(2F,3F)-O2 | (2-8) | 20% |
| 2-HH-3 | (3-1) | 20% |
| 3-HH-4 | (3-1) | 6% |
| 1-BB-3 | (3-3) | 7% |
| 3-HHB-O1 | (3-5) | 3% |
| 3-HHB-1 | (3-5) | 3% |
| 3-HHB-3 | (3-5) | 3% |

NI = 74.0° C.; Tc < −20° C.; Δn = 0.108; Δ∈ = −3.3; Vth = 2.22 V; η = 17.6 mPa·s.

Comparative Example 1

In Example 1, the first component is compound (1-1). For comparison, a composition was prepared in which the first component was not included. That is to say, 1-B2BB-2V in the composition of Example 1 was replaced by 1-BBB-2V. The reason is that this compound belongs to compound (3) of the third component and has a similar structure.

| 1-BBB-2V | (3) | 8% |
| --- | --- | --- |
| 3-BB(2F,3F)-O2 | (2-4) | 12% |
| 5-BB(2F,3F)-O2 | (2-4) | 8% |
| 2-HH1OB(2F,3F)-O2 | (2-8) | 10% |
| 3-HH1OB(2F,3F)-O2 | (2-8) | 20% |
| 2-HH-3 | (3-1) | 20% |
| 3-HH-4 | (3-1) | 6% |
| 1-BB-3 | (3-3) | 7% |
| 3-HHB-O1 | (3-5) | 3% |
| 3-HHB-1 | (3-5) | 3% |
| 3-HHB-3 | (3-5) | 3% |

Tc > 25° C. (crystals deposited at 25° C.)

Example 2

| 1-B2BB-2V | (1-1) | 7% |
| --- | --- | --- |
| V-HB(2F,3F)-O2 | (2-1) | 4% |
| 3-HB(2F,3F)-O2 | (2-1) | 6% |
| 3-H1O(2F,3F)-O2 | (2-3) | 10% |
| 3-BB(2F,3F)-O2 | (2-4) | 8% |
| 5-B(2F,3F)B(2F,3F)-O2 | (2-5) | 4% |
| 3-HH1OB(2F,3F)-O2 | (2-8) | 14% |
| 3-HH-V | (3-1) | 16% |
| 4-HH-V1 | (3-1) | 9% |
| 1V2-BB-1 | (3-3) | 4% |
| V-HHB-1 | (3-5) | 8% |
| V2-HHB-1 | (3-5) | 5% |
| V-HBB-2 | (3-6) | 5% |

NI = 71.6° C.; Tc < −20° C.; Δn = 0.108; Δ∈ = −3.0; Vth = 2.26 V; η = 10.6 mPa·s.

Example 3

| 3-B2B(2F)B-3 | (1-2) | 5% |
| --- | --- | --- |
| 3-B2BB(2F)-3 | (1-4) | 3% |
| 3-H2B(2F,3F)-O2 | (2-2) | 4% |
| 5-H2B(2F,3F)-O2 | (2-2) | 4% |
| 3-BB(2F,3F)-O2 | (2-4) | 7% |
| 5-BB(2F,3F)-O2 | (2-4) | 4% |
| 3-HH1OB(2F,3F)-O2 | (2-8) | 14% |
| 3-H1OCro(7F,8F)-5 | (2-18) | 5% |
| 3-HH1OCro(7F,8F)-5 | (2-19) | 8% |
| 3-HH-V | (3-1) | 11% |
| 1V2-HH-3 | (3-1) | 5% |
| 2-HH-3 | (3-1) | 12% |
| 3-HB-O2 | (3-2) | 5% |
| 3-HHEH-3 | (3-4) | 4% |
| 3-HHEH-5 | (3-4) | 4% |
| V-HHB-1 | (3-5) | 5% |

NI = 72.8° C.; Tc < −20° C.; Δn = 0.089; Δ∈ = −3.4; Vth = 2.20 V; η = 20.6 mPa·s.

Example 4

| 3-B2B(F)B-3 | (1-3) | 8% |
| --- | --- | --- |
| V-HB(2F,3F)-O2 | (2-1) | 4% |
| 3-BB(2F,3F)-O2 | (2-4) | 11% |
| 5-BB(2F,3F)-O2 | (2-4) | 6% |
| V2-HHB(2F,3F)-O2 | (2-6) | 7% |
| 2-HH1OB(2F,3F)-O2 | (2-8) | 5% |
| 3-HH1OB(2F,3F)-O2 | (2-8) | 6% |
| 3-dhBB(2F,3F)-O2 | (2-14) | 5% |
| 3-HBB(2F,3Cl)-02 | (2-17) | 4% |
| 3-HH-V | (3-1) | 18% |
| 1V2-HH-1 | (3-1) | 3% |
| 2-HH-3 | (3-1) | 6% |
| VFF2-HHB-1 | (3-5) | 3% |
| 3-HBB-2 | (3-6) | 4% |
| 5-B(F)BB-2 | (3-8) | 4% |
| 5-HBB(F)B-2 | (3-13) | 3% |
| 1O1-HBBH-5 | (—) | 3% |

NI = 85.8° C.; Tc < −20° C.; Δn = 0.124; Δ∈ = −3.0; Vth = 2.25 V; η = 18.4 mPa·s.

Example 5

| 1-B2BB-3 | (1-1) | 4% |
| --- | --- | --- |
| 3-B2B(2F)B-3 | (1-2) | 5% |
| 3-H1OB(2F,3F)-O2 | (2-3) | 9% |
| 3-HH2B(2F,3F)-O2 | (2-7) | 7% |
| 3-HH1OB(2F,3F)-O2 | (2-8) | 9% |
| 2-BB(2F,3F)B-4 | (2-9) | 4% |
| 3-DhhB(2F,3F)-O2 | (2-10) | 6% |
| V-HBB(2F,3F)-O2 | (2-13) | 6% |
| 3-HHB(2F,3Cl)-02 | (2-16) | 6% |
| 3-HH-V | (3-1) | 18% |
| 3-HH-V1 | (3-1) | 7% |
| 5-HH-V | (3-1) | 6% |
| V2-BB-1 | (3-3) | 5% |
| 2-BB(F)B-3 | (3-7) | 4% |
| 3-HB(F)HH-2 | (3-9) | 4% |

NI = 91.0° C.; Tc < −20° C.; Δn = 0.112; Δ∈ = −3.0; Vth = 2.28 V; η = 15.5 mPa·s.

Example 6

| 3-B2B(2F)B-3 | (1-2) | 4% |
| --- | --- | --- |
| V2-B2B(F)B-3 | (1-3) | 4% |
| 3-B2BB(2F)-3 | (1-4) | 3% |
| 3-H1OB(2F,3F)-O2 | (2-3) | 7% |
| 5-B(2F,3F)B(2F,3F)-O2 | (2-5) | 3% |
| V-HHB(2F,3F)-O2 | (2-6) | 8% |
| 3-HDhB(2F,3F)-O2 | (2-11) | 5% |
| 3-HBB(2F,3F)-O2 | (2-13) | 5% |
| 5-HHB(2F,3Cl)-02 | (2-16) | 4% |
| 5-HBB(2F,3Cl)-02 | (2-17) | 4% |
| 3-HH-V | (3-1) | 16% |
| 3-HH-V1 | (3-1) | 7% |
| 3-HH-4 | (3-1) | 7% |
| 1-BB-3 | (3-3) | 8% |
| 3-HHB-1 | (3-5) | 3% |
| 3-HHB-3 | (3-5) | 3% |
| 1-BB(F)B-2V | (3-7) | 3% |

-continued

| | | |
|---|---|---|
| 2-BB(F)B-2V | (3-7) | 3% |
| 3-HHEBH-5 | (3-10) | 3% |

NI = 88.2° C.; Tc < −20° C.; Δn = 0.116; Δ∈ = −2.7; Vth = 2.30 V; η = 16.1 mPa·s.

Example 7

| | | |
|---|---|---|
| 1-B2BB-2V | (1-1) | 9% |
| 5-BB(2F,3F)-O2 | (2-4) | 8% |
| 2-HH1OB(2F,3F)-O2 | (2-8) | 10% |
| 3-HH1OB(2F,3F)-O2 | (2-8) | 19% |
| 2-BB(2F,3F)B-3 | (2-9) | 9% |
| 2-BB(2F,3F)B-4 | (2-9) | 7% |
| 3-HH-V | (3-1) | 15% |
| 4-HH-V | (3-1) | 10% |
| F3-HH-V1 | (3-1) | 3% |
| V-HHB-1 | (3-5) | 5% |
| V2-HHB-1 | (3-5) | 5% |

NI = 96.7° C.; Tc < −20° C.; Δn = 0.125; Δ∈ = −3.0; Vth = 2.28 V; η = 15.9 mPa·s.

Example 8

| | | |
|---|---|---|
| 1-B2BB-2V | (1-1) | 4% |
| 3-B2BB(2F)-3 | (1-4) | 4% |
| 3-HB(2F,3F)-O2 | (2-1) | 8% |
| 3-BB(2F,3F)-O2 | (2-4) | 11% |
| V2-BB(2F,3F)-O2 | (2-4) | 5% |
| 2-HH1OB(2F,3F)-O2 | (2-8) | 7% |
| 3-HH1OB(2F,3F)-O2 | (2-8) | 10% |
| 3-H1OCro(7F,8F)-5 | (2-18) | 6% |
| 3-HH-V | (3-1) | 20% |
| 3-HH-V1 | (3-1) | 10% |
| V-HHB-1 | (3-5) | 8% |
| 5-HBBH-3 | (3-11) | 3% |
| 5-HB(F)BH-3 | (3-12) | 4% |

NI = 79.4° C.; Tc < −20° C.; Δn = 0.105; Δ∈ = −3.3; Vth = 2.24 V; η = 16.6 mPa·s.

Example 9

| | | |
|---|---|---|
| 1-B2BB-3 | (1-1) | 3% |
| 3-B2B(F)B-3 | (1-3) | 3% |
| 3-BB(2F,3F)-O2 | (2-4) | 6% |
| 3-HHB(2F,3F)-O2 | (2-6) | 5% |
| V-HHB(2F,3F)-O2 | (2-6) | 5% |
| 3-HH2B(2F,3F)-O2 | (2-7) | 3% |
| 3-HH1OB(2F,3F)-O2 | (2-8) | 14% |
| 3-HDhB(2F,3F)-O2 | (2-11) | 7% |
| 3-DhH1OB(2F,3F)-O2 | (2-12) | 8% |
| 3-HH-VFF | (3-1) | 4% |
| 2-HH-3 | (3-1) | 20% |
| 3-HH-4 | (3-1) | 5% |
| V2-BB-1 | (3-3) | 4% |
| VFF-HHB-1 | (3-5) | 3% |
| V-HHB-1 | (3-5) | 4% |
| V2-HHB-1 | (3-5) | 3% |
| 2-BB(F)B-2V | (3-7) | 3% |

NI = 92.8° C.; Tc < −20° C.; Δn = 0.100; Δ∈ = −2.9; Vth = 2.27 V; η = 17.6 mPa·s.

Example 10

| | | |
|---|---|---|
| 3-B2B(2F)B-3 | (1-2) | 8% |
| 3-BB(2F,3F)-O2 | (2-4) | 10% |
| 5-BB(2F,3F)-O2 | (2-4) | 7% |
| 2-HH1OB(2F,3F)-O2 | (2-8) | 7% |
| 3-HH1OB(2F,3F)-O2 | (2-8) | 9% |
| 3-HEB(2F,3F)B(2F,3F)-O2 | (2-15) | 3% |
| 3-HBB(2F,3Cl)-O2 | (2-17) | 4% |
| 3-HH-V | (3-1) | 20% |
| 3-HH-V1 | (3-1) | 11% |
| F3-HH-V | (3-1) | 4% |
| 1V2-BB-1 | (3-3) | 4% |
| V-HBB-3 | (3-6) | 3% |
| 2-BB(F)B-5 | (3-7) | 4% |
| 5-B(F)BB-3 | (3-8) | 3% |
| 1O1-HBBH-5 | (—) | 3% |

NI = 80.5° C.; Tc < −20° C.; Δn = 0.121; Δ∈ = −2.7; Vth = 2.30 V; η = 12.6 mPa·s.

Example 11

| | | |
|---|---|---|
| 3-B2B(F)B-3 | (1-3) | 6% |
| 3-B2BB(2F)-3 | (1-4) | 6% |
| 3-BB(2F,3F)-O2 | (2-4) | 10% |
| 2O-BB(2F,3F)-O2 | (2-4) | 5% |
| 2-HH1OB(2F,3F)-O2 | (2-8) | 11% |
| 3-HH1OB(2F,3F)-O2 | (2-8) | 18% |
| 5-HH-VFF | (3-1) | 3% |
| 4-HH-V | (3-1) | 10% |
| 4-HH-V1 | (3-1) | 8% |
| 5-HB-O2 | (3-2) | 4% |
| 7-HB-1 | (3-2) | 5% |
| 1-BB(F)B-2V | (3-7) | 4% |
| 3-BB(F)B-2V | (3-7) | 4% |
| 3-HHEBH-3 | (3-10) | 3% |
| 3-HHEBH-4 | (3-10) | 3% |

NI = 93.1° C.; Tc < −20° C.; Δn = 0.121; Δ∈ = −2.9; Vth = 2.29 V; η = 19.4 mPa·s.

In Examples 1 to 11, the minimum temperatures (Tc) of the compositions were all lower than −20° C. In contrast, crystals deposited at room temperature (25° C.) in the composition of Comparative Example 1, which means a minimum temperature higher than 25° C. Accordingly, the compositions in Examples had a low minimum temperature in comparison with that in Comparative Example 1. Thus, it is concluded that the liquid crystal composition of the invention has a superior characteristics.

INDUSTRIAL APPLICABILITY

The liquid crystal composition of the invention satisfies at least one of characteristics such as a high maximum temperature, a low minimum temperature, a small viscosity, a suitable optical anisotropy, a large negative dielectric anisotropy, a large specific resistance, a high stability to UV light and a high stability to heat, or is suitably balanced between at least two of the characteristics. A liquid crystal display device including this composition can be used for a liquid crystal projector, a liquid crystal television and so forth, since it has characteristics such as a short response time, a large voltage holding ratio, a low threshold voltage, a large contrast ratio and a long service life.

The invention claimed is:
1. A liquid crystal composition, having a negative dielectric anisotropy, and comprising at least one compound selected from the group of compounds represented by formula (1) as a first component and at least one compound selected from the group of compounds represented by formula (2) as a second component:

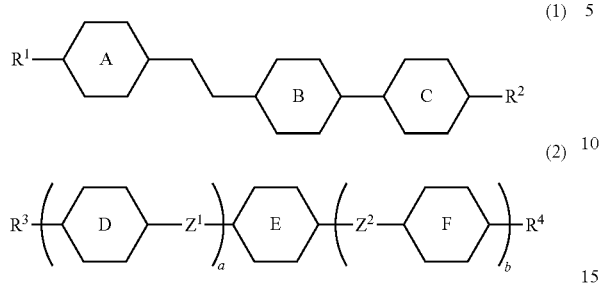

wherein
in formula (1), R$^1$ and R$^2$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen; and ring A, ring B and ring C are independently 1,4-phenylene, or 1,4-phenylene in which at least one hydrogen has been replaced by fluorine or chlorine, and in formula (2), R$^3$ and R$^4$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen has been replaced by halogen; ring D and ring F are independently 1,4-cyclohexylene, 1,4-cyclohexenylene, 1,4-phenylene, 1,4-phenylene in which at least one hydrogen has been replaced by fluorine or chlorine, or tetrahydropyran-2,5-diyl; ring E is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; Z$^1$ and Z$^2$ are independently a single bond, ethylene, carbonyloxy or methyleneoxy; a is 1, 2 or 3; b is 0 or 1; the sum of a and b is 3 or less; and when the sum of a and b is 2, and the a-numbering ring D and the b-numbering ring F are 1,4-phenylene, or 1,4-phenylene in which at least one hydrogen has been replaced by fluorine or chlorine, Z$^1$ and Z$^2$ are independently a single bond, carbonyloxy or methyleneoxy.

2. The liquid crystal composition of claim 1, comprising at least one compound selected from the group of compounds represented by formulae (1-1) to (1-4) as the first component:

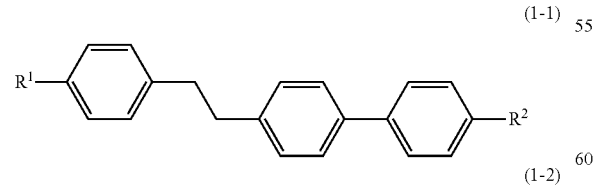

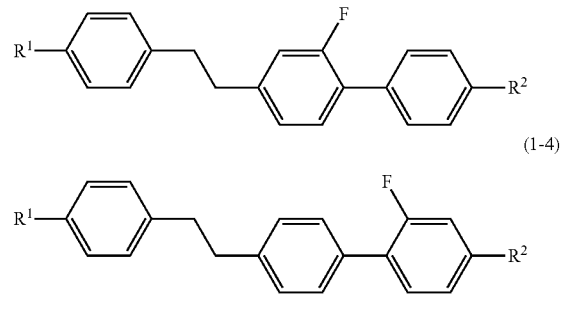

wherein in formulae (1-1) to (1-4), R$^1$ and R$^2$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen.

3. The liquid crystal composition of claim 1, wherein a proportion of the first component is in a range of 3 wt % to 20 wt % based on a weight of the liquid crystal composition.

4. The liquid crystal composition of claim 1, comprising at least one compound selected from the group of compounds represented by formula (2-1) to formula (2-19) as the second component:

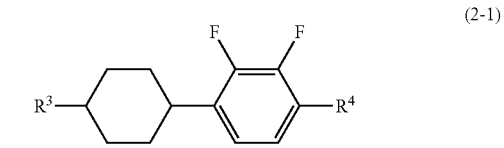

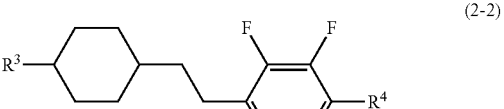

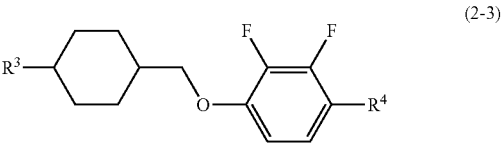

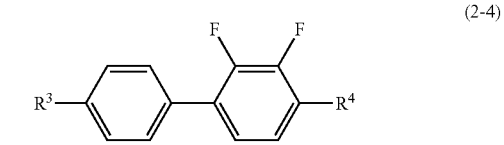

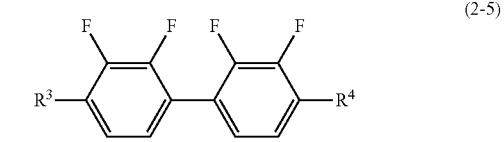

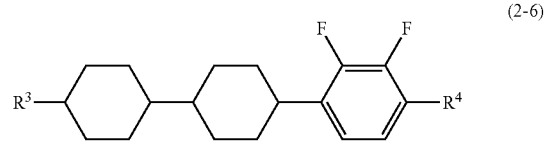

(2-7)
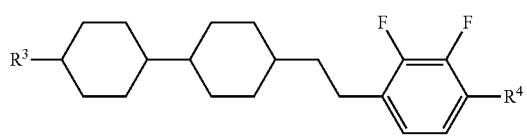

(2-8)
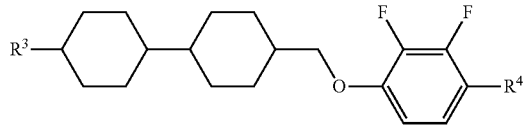

(2-9)
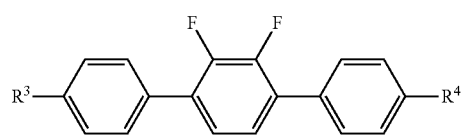

(2-10)
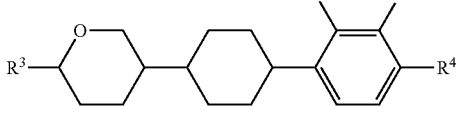

(2-11)
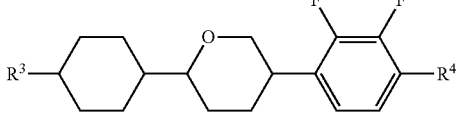

(2-12)
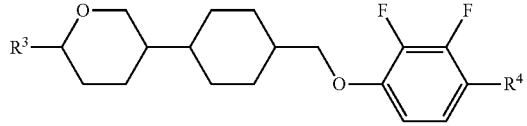

(2-13)
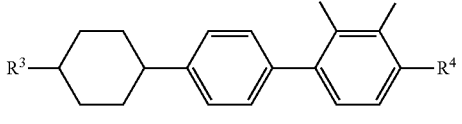

(2-14)
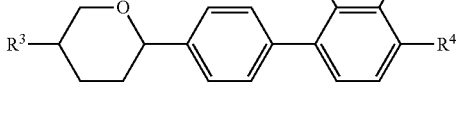

(2-15)
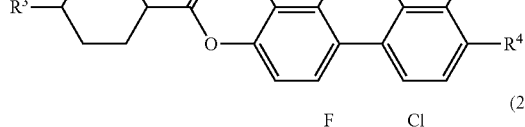

(2-16)
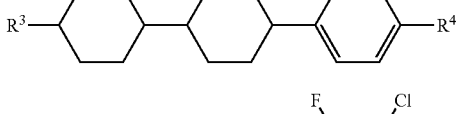

(2-17)

(2-18)
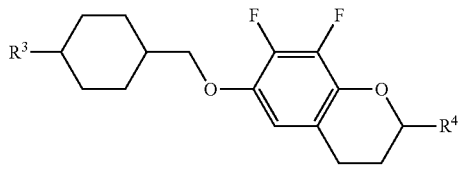

(2-19)
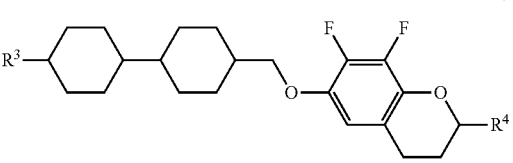

wherein in formulae (2-1) to (2-19), $R^3$ and $R^4$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one hydrogen has been replaced by halogen.

5. The liquid crystal composition of claim 1, wherein a proportion of the second component is in a range of 20 wt % to 70 wt % based on a weight of the liquid crystal composition.

6. The liquid crystal composition of claim 1, further comprising at least one compound selected from the group of compounds represented by formula (3) as a third component:

(3)
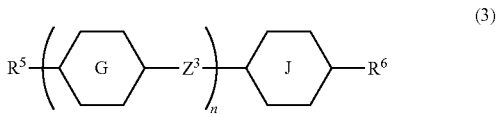

wherein in formula (3), $R^5$ and $R^6$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen; ring G and ring J are independently 1,4-cyclohexylene, 1,4-phenylene, 2-fluoro-1,4-phenylene or 2,5-difluoro-1,4-phenylene; $Z^3$ is a single bond, ethylene or carbonyloxy; n is 1, 2 or 3; and when n is 2, and two of rings G and ring J are 1,4-phenylene, 2-fluoro-1,4-phenylene or 2,5-difluoro-1,4-phenylene, $Z^3$ is a single bond or carbonyloxy.

7. The liquid crystal composition of claim 6, comprising at least one compound selected from the group of compounds represented by formula (3-1) to formula (3-13) as the third component:

(3-1)
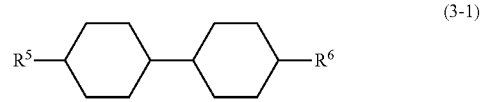

(3-2)
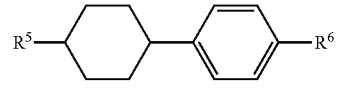

-continued (3-3)

R⁵—⟨phenyl⟩—⟨phenyl⟩—R⁶

(3-4)

R⁵—⟨cyclohexyl⟩—⟨cyclohexyl⟩—C(=O)O—⟨cyclohexyl⟩—R⁶

(3-5)

R⁵—⟨cyclohexyl⟩—⟨cyclohexyl⟩—⟨phenyl⟩—R⁶

(3-6)

R⁵—⟨cyclohexyl⟩—⟨phenyl⟩—⟨phenyl⟩—R⁶

(3-7)

R⁵—⟨phenyl⟩—⟨phenyl-F⟩—⟨phenyl⟩—R⁶

(3-8)

R⁵—⟨phenyl-F⟩—⟨phenyl⟩—⟨phenyl⟩—R⁶

(3-9)

R⁵—⟨cyclohexyl⟩—⟨phenyl-F⟩—⟨cyclohexyl⟩—⟨cyclohexyl⟩—R⁶

(3-10)

R⁵—⟨cyclohexyl⟩—⟨cyclohexyl⟩—C(=O)O—⟨phenyl⟩—⟨cyclohexyl⟩—R⁶

(3-11)

R⁵—⟨cyclohexyl⟩—⟨phenyl⟩—⟨phenyl⟩—⟨cyclohexyl⟩—R⁶

(3-12)

R⁵—⟨cyclohexyl⟩—⟨phenyl-F⟩—⟨phenyl⟩—⟨cyclohexyl⟩—R⁶

(3-13)

R⁵—⟨cyclohexyl⟩—⟨phenyl⟩—⟨phenyl-F⟩—⟨cyclohexyl⟩—R⁶ wherein in formulae (3-1) to (3-13), $R^5$ and $R^6$ are independently alkyl having 1 to 12 carbons, alkoxy having 1 to 12 carbons, alkenyl having 2 to 12 carbons, alkyl having 1 to 12 carbons in which at least one hydrogen has been replaced by halogen, or alkenyl having 2 to 12 carbons in which at least one hydrogen has been replaced by halogen.

8. The liquid crystal composition of claim 6, wherein a proportion of the third component is in a range of 20 wt % to 70 wt % based on a weight of the liquid crystal composition.

9. The liquid crystal composition of claim 1, further comprising at least one polymerizable compound selected from the group of compounds represented by formula (4) as an additive component:

(4)

$$\left(\begin{array}{c}P^1\\|\\Sp^1\end{array}\right)_h \quad K - Z^4 - \left(\begin{array}{c}\left(\begin{array}{c}P^2\\|\\Sp^2\end{array}\right)_j\\L\end{array} - Z^5\right)_g - \left(\begin{array}{c}P^3\\|\\Sp^3\end{array}\right)_k \quad M$$

wherein in formula (4), ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; $Z^4$ and $Z^5$ are independently a single bond or alkylene having 1 to 10 carbons, and in the alkylene at least one —CH₂— may be replaced by —O—, —CO—, —COO— or —OCO—, at least one —CH₂—CH₂— may be replaced by —CH=CH—, —C(CH₃)=CH—, —CH=C(CH₃)— or —C(CH₃)=C(CH₃)—, and in these groups at least one hydrogen may be replaced by fluorine or chlorine; $P^1$, $P^2$ and a $P^3$ are independently a polymerizable group; $Sp^1$, $Sp^2$ and $Sp^3$ are independently a single bond or alkylene having 1 to 10 carbons, and in the alkylene, at least one —CH₂— may be replaced by —O—, —COO—, —OCO— or —OCOO—, at least one —CH₂—CH₂— may be replaced by —CH=CH— or —C≡C—, and in these groups at least one hydrogen may be replaced by fluorine or chlorine; g is 0, 1 or 2; h, j and k are independently 0, 1, 2, 3 or 4; and the sum of h, j and k is 1 or more.

10. The liquid crystal composition of claim 9, wherein in formula (4), $P^1$, $P^2$ and $P^3$ are independently a polymerizable group selected from the group of groups represented by formulae (P-1) to (P-6):

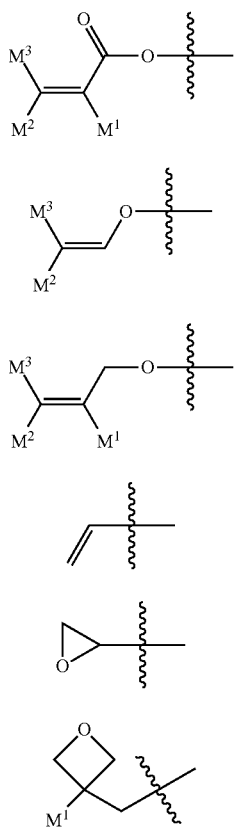

(P-1)
(P-2)
(P-3)
(P-4)
(P-5)
(P-6)

alkyl having 1 to 5 carbons, or alkyl having 1 to 5 carbons in which at least one hydrogen has been replaced by halogen; and in formula (4), at least one of the h-numbering $Sp^1$ and the k-numbering $Sp^3$ is alkylene in which at least one —$CH_2$— has been replaced by —O—, —COO—, —OCO— or —OCOO— when all of the h-numbering $P^1$ and the k-numbering $P^3$ are a group represented by formula (P-4).

11. The liquid crystal composition of claim 9, comprising at least one polymerizable compound selected from the group of compounds represented by formulae (4-1) to (4-27) as the additive component:

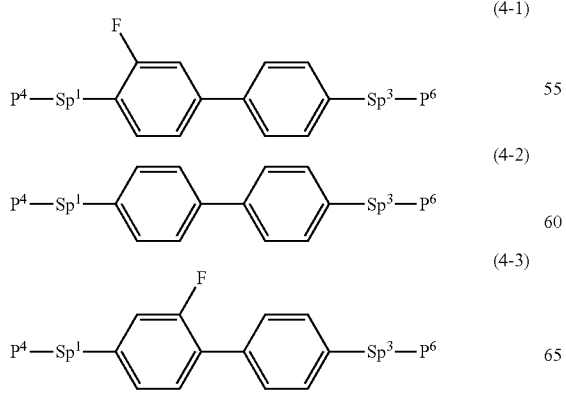

(4-1)
(4-2)
(4-3)

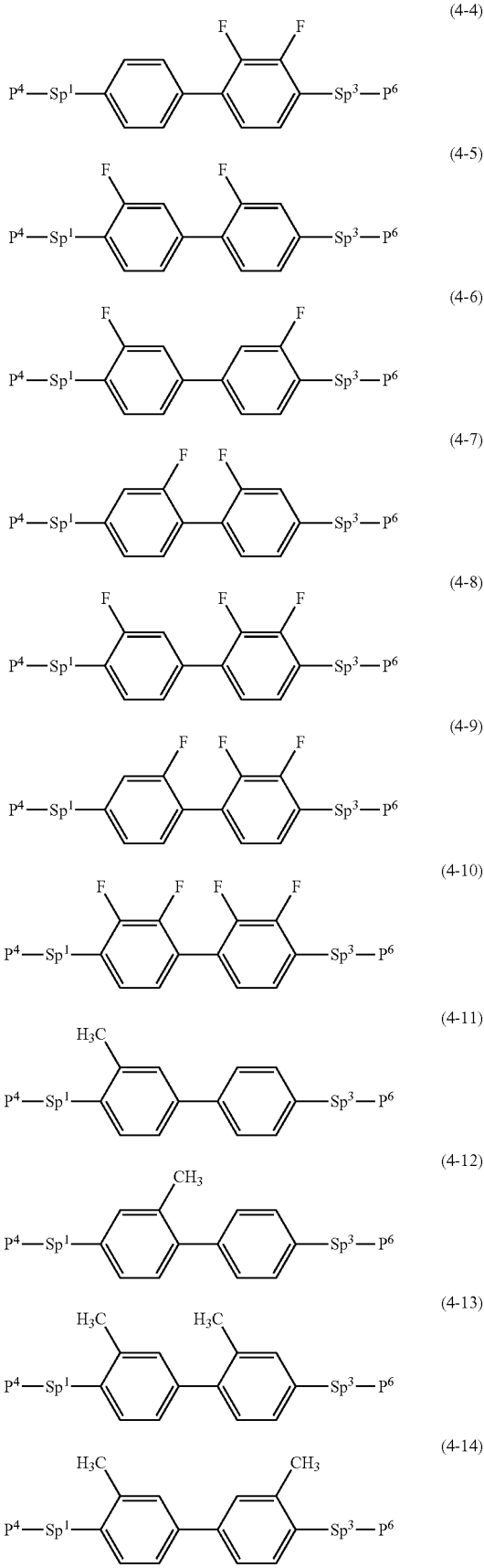

(4-4)
(4-5)
(4-6)
(4-7)
(4-8)
(4-9)
(4-10)
(4-11)
(4-12)
(4-13)
(4-14)

(4-15)
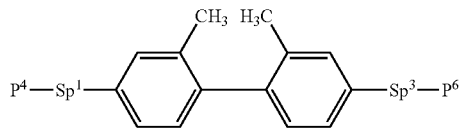

(4-16)
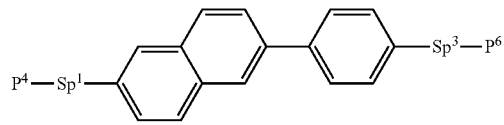

(4-17)
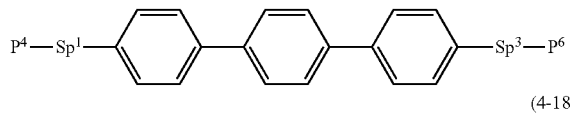

(4-18)
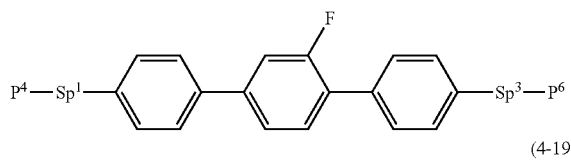

(4-19)
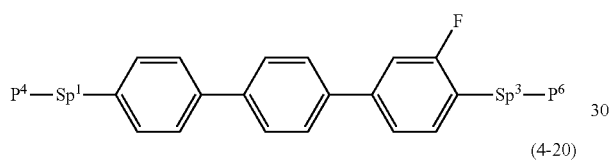

(4-20)
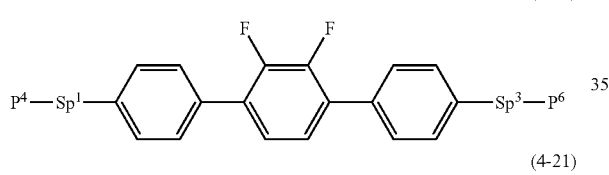

(4-21)
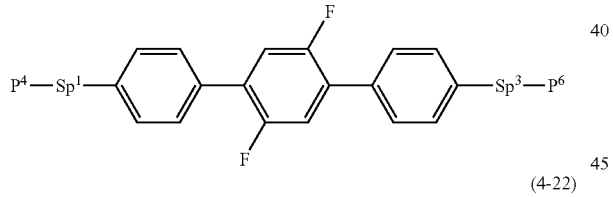

(4-22)
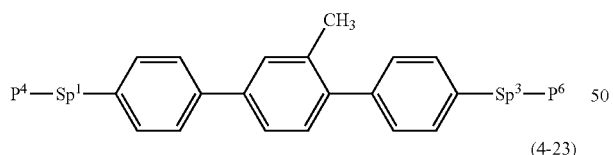

(4-23)
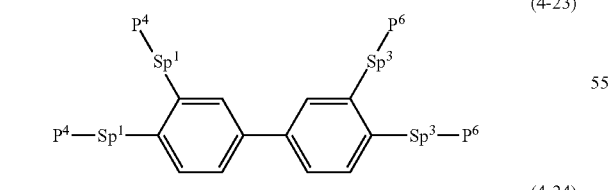

(4-24)
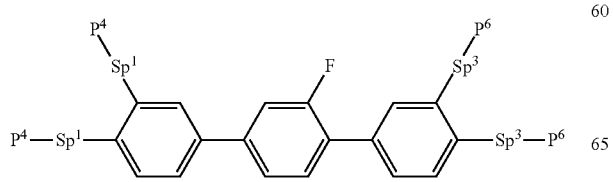

(4-25)
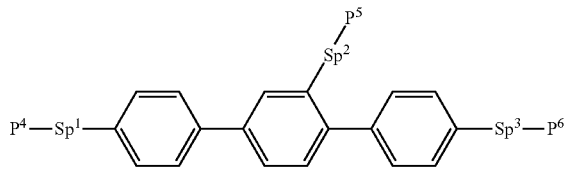

(4-26)
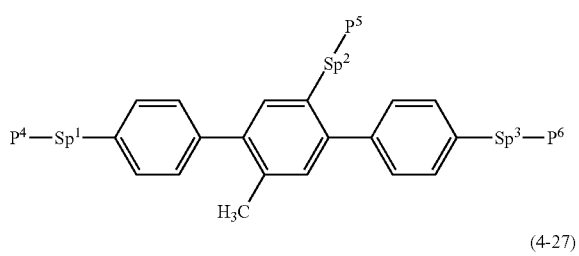

(4-27)
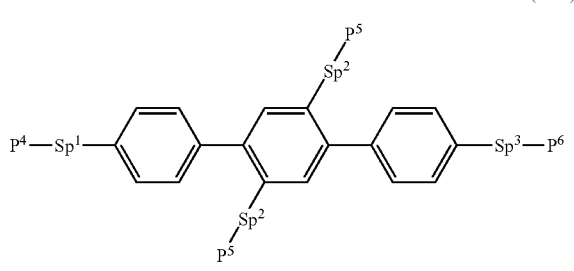

wherein in formulae (4-1) to (4-27), $P^4$, $P^5$ and $P^6$ are independently a polymerizable group selected from the group of groups represented by formulae (P-1) to (P-3);

(P-1)
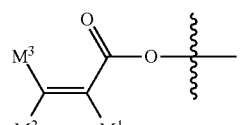

(P-2)
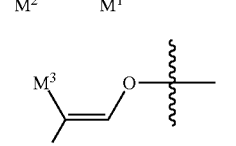

(P-3)
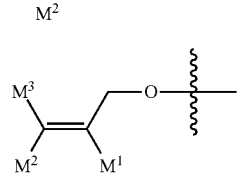

in formulae (P-1) to (P-3), $M^1$, $M^2$ and $M^3$ are independently hydrogen, fluorine, alkyl having 1 to 5 carbons, or alkyl having 1 to 5 carbons in which at least one hydrogen has been replaced by halogen; and in formulae (4-1) to (4-27), $Sp^1$, $Sp^2$ and $Sp^a$ are independently a single bond or alkylene having 1 to 10 carbons, and in the alkylene at least one —CH$_2$— may be replaced by —O—, —COO—, —OCO— or —OCOO—, at least one —CH$_2$—CH$_2$— may be replaced by —CH=CH— or —C≡C—, and in these groups at least one hydrogen may be replaced by fluorine or chlorine.

12. The liquid crystal composition of claim 9, wherein a proportion of the additive component is in a range of 0.03 wt % to 10 wt % based on a weight of the liquid crystal composition.

13. The liquid crystal composition of claim 6, further comprising at least one polymerizable compound selected from the group of compounds represented by formula (4) as an additive component:

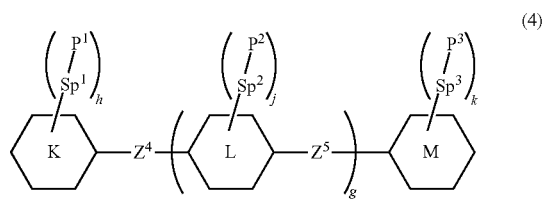

(4)

wherein in formula (4), ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; ring L is 1,4-cyclohexylene, 1,4-cyclohexenylene, 1,4-phenyl ene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in these rings at least one hydrogen may be replaced by halogen, alkyl having 1 to 12 carbons, alkoxy having 1 to 12 carbons, or alkyl having 1 to 12 carbons in which at least one hydrogen has been replaced by halogen; $Z^4$ and $Z^5$ are independently a single bond or alkylene having 1 to 10 carbons, and in the alkylene at least one —$CH_2$— may be replaced by —O—, —CO—, —COO— or —OCO—, at least one —$CH_2$—$CH_2$— may be replaced by —CH=CH—, —C($CH_3$)=CH—, —CH=C($CH_3$)— or —C($CH_3$)=C($CH_3$)—, and in these groups at least one hydrogen may be replaced by fluorine or chlorine; $P^1$, $P^2$ and $P^3$ are a polymerizable group; $Sp^1$, $Sp^2$ and $Sp^a$ are independently a single bond or alkylene having 1 to 10 carbons, and in the alkylene, at least one —$CH_2$— may be replaced by —O—, —COO—, —OCO— or —OCOO—, at least one —$CH_2$—$CH_2$— may be replaced by —CH=CH— or —C≡C—, and in these groups at least one hydrogen may be replaced by fluorine or chlorine; g is 0, 1 or 2; h, j and k are independently 0, 1, 2, 3 or 4; and the sum of h, j and k is 1 or more.

14. A liquid crystal display device comprising the liquid crystal composition of claim 1.

15. The liquid crystal display device of claim 14, wherein the operating mode of the liquid crystal display device is an IPS mode, a VA mode, an FFS mode or an FPA mode, and the driving mode of the liquid crystal display device is an active matrix mode.

16. A liquid crystal display device with a polymer sustained alignment type, comprising the liquid crystal composition of claim 9, or comprising the liquid crystal composition in which a polymerizable compound has been polymerized.

* * * * *